US012502276B2

(12) United States Patent
Nelson et al.

(10) Patent No.: US 12,502,276 B2
(45) Date of Patent: Dec. 23, 2025

(54) INVERSION DELIVERY DEVICE AND METHOD FOR A PROSTHESIS

(71) Applicant: EDWARDS LIFESCIENCES CORPORATION, Irvine, CA (US)

(72) Inventors: Dale K. Nelson, Inver Grove Heights, MN (US); John P. Gainor, Mendota Heights, MN (US); Evan M. Leingang, Plymouth, MN (US); Robert Foster Wilson, Roseville, MN (US); Cassandra Ann Piippo Svendsen, Blaine, MN (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 615 days.

(21) Appl. No.: 17/813,303

(22) Filed: Jul. 18, 2022

(65) Prior Publication Data

US 2022/0346952 A1 Nov. 3, 2022

Related U.S. Application Data

(60) Continuation of application No. 16/384,707, filed on Apr. 15, 2019, now Pat. No. 11,413,143, which is a (Continued)

(51) Int. Cl.
*A61F 2/24* (2006.01)
*A61F 2/95* (2013.01)

(52) U.S. Cl.
CPC .......... *A61F 2/2439* (2013.01); *A61F 2/2418* (2013.01); *A61F 2/2427* (2013.01); (Continued)

(58) Field of Classification Search
CPC .... A61F 2/2418; A61F 2/2427; A61F 2/2436; A61F 2/2439; A61F 2/2466; A61F 2/06; (Continued)

(56) References Cited

U.S. PATENT DOCUMENTS 3,409,013 A 11/1968 Berry
3,472,230 A 10/1969 Fogarty
(Continued)

FOREIGN PATENT DOCUMENTS

CA 2304325 C 5/2008
CN 1870950 A 11/2006
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Ashley L Fishback
(74) *Attorney, Agent, or Firm* — Thomas C. Richardson

(57) ABSTRACT

A delivery device usable to deliver an inverting implant is provided that includes a positioning mechanism that automatically initiates the inversion process once a predetermined length of the implant has exited a delivery catheter. The positioning mechanism allows the implant to be safely and accurately deployed with reduced operator experience and in a greater variety of target locations.

20 Claims, 22 Drawing Sheets

Related U.S. Application Data continuation of application No. 15/370,009, filed on Dec. 6, 2016, now Pat. No. 10,278,817, which is a division of application No. 14/270,286, filed on May 5, 2014, now Pat. No. 9,693,863, and a division of application No. 14/270,300, filed on May 5, 2014, now Pat. No. 9,795,478, said application No. 14/270,286 is a continuation of application No. 13/657,800, filed on Oct. 22, 2012, now Pat. No. 9,522,064, said application No. 14/270,300 is a continuation of application No. 13/657,800, filed on Oct. 22, 2012, now Pat. No. 9,522,064, which is a continuation-in-part of application No. 13/473,475, filed on May 16, 2012, now abandoned.

(60) Provisional application No. 61/486,682, filed on May 16, 2011.

(52) U.S. Cl.
CPC .......... *A61F 2/2436* (2013.01); *A61F 2/9517* (2020.05); *A61F 2002/9534* (2013.01)

(58) Field of Classification Search
CPC ... A61F 2/95; A61F 2/9517; A61F 2002/9534
See application file for complete search history.

(56) References Cited

U.S. PATENT DOCUMENTS 3,548,417 A 12/1970 Kischer et al.
3,587,115 A 6/1971 Shiley
3,657,744 A 4/1972 Ersek
3,671,979 A 6/1972 Moulopoulos
3,714,671 A 2/1973 Edwards et al.
3,739,402 A 6/1973 Cooley et al.
3,755,823 A 9/1973 Hancock
4,011,947 A 3/1977 Sawyer
4,035,849 A 7/1977 Angell et al.
4,056,854 A 11/1977 Boretos et al.
4,079,468 A 3/1978 Liotta et al.
4,106,129 A 8/1978 Carpentier et al.
4,204,283 A 5/1980 Bellhouse et al.
4,222,126 A 9/1980 Boretos et al.
4,265,694 A 5/1981 Boretos et al.
4,297,749 A 11/1981 Davis et al.
4,339,831 A 7/1982 Johnson
4,340,977 A 7/1982 Brownlee et al.
4,343,048 A 8/1982 Ross et al.
4,345,340 A 8/1982 Rosen
4,373,216 A 2/1983 Klawitter
4,406,022 A 9/1983 Roy
4,470,157 A 9/1984 Love
4,477,930 A 10/1984 Totten et al.
4,490,859 A 1/1985 Black et al.
4,535,483 A 8/1985 Klawitter et al.
4,553,545 A 11/1985 Maass et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,829,990 A 5/1989 Thuroff et al.
4,851,001 A 7/1989 Taheri
4,856,516 A 8/1989 Hillstead
4,865,600 A 9/1989 Carpentier et al.
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,108,370 A 4/1992 Walinsky
5,152,771 A 10/1992 Sabbaghian et al.
5,163,953 A 11/1992 Vince
5,167,628 A 12/1992 Boyles
5,192,297 A 3/1993 Hull
5,232,446 A 8/1993 Arney
5,266,073 A 11/1993 Wall
5,282,847 A 2/1994 Trescony et al.
5,295,958 A 3/1994 Shturman
5,326,371 A 7/1994 Love et al.
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,522 A 5/1995 Trott
5,411,552 A 5/1995 Andersen et al.
5,415,667 A 5/1995 Frater
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,571,175 A 11/1996 Vanney et al.
5,591,185 A 1/1997 Kilmer et al.
5,599,305 A 2/1997 Hermann et al.
5,607,464 A 3/1997 Trescony et al.
5,609,626 A 3/1997 Quijano et al.
5,639,274 A 6/1997 Fischell et al.
5,665,115 A 9/1997 Cragg
5,697,382 A 12/1997 Love et al.
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,906,619 A 5/1999 Olson et al.
5,925,063 A 7/1999 Khosravi
5,957,949 A 9/1999 Leonhardt et al.
5,968,068 A 10/1999 Dehdashtian et al.
6,027,525 A 2/2000 Suh et al.
6,042,607 A 3/2000 Williamson et al.
6,086,612 A 7/2000 Jansen
6,113,631 A 9/2000 Jansen
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,040 B1 6/2001 Inderbitzen et al.
6,245,102 B1 6/2001 Jayaraman

(56) References Cited

U.S. PATENT DOCUMENTS

| | | | |
|---|---|---|---|
| 6,251,093 | B1 | 6/2001 | Valley et al. |
| 6,287,339 | B1 | 9/2001 | Vazquez et al. |
| 6,299,637 | B1 | 10/2001 | Shaolian et al. |
| 6,302,906 | B1 | 10/2001 | Goicoechea et al. |
| 6,306,141 | B1 | 10/2001 | Jervis |
| 6,312,465 | B1 | 11/2001 | Griffin et al. |
| 6,338,740 | B1 | 1/2002 | Carpentier |
| 6,350,277 | B1 | 2/2002 | Kocur |
| 6,358,277 | B1 | 3/2002 | Duran |
| 6,379,372 | B1 | 4/2002 | Dehdashtian et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,800 | B1 | 3/2003 | McGuckin et al. |
| 6,527,979 | B2 | 3/2003 | Constantz et al. |
| 6,540,782 | B1 | 4/2003 | Snyders |
| 6,569,196 | B1 | 5/2003 | Vesely |
| 6,575,959 | B1 | 6/2003 | Sarge et al. |
| 6,582,462 | B1 | 6/2003 | Andersen et al. |
| 6,605,112 | B1 | 8/2003 | Moll et al. |
| 6,610,088 | B1 | 8/2003 | Gabbay |
| 6,629,534 | B1 | 10/2003 | St. Goar et al. |
| 6,676,698 | B2 | 1/2004 | McGuckin et al. |
| 6,695,878 | B2 | 2/2004 | McGuckin et al. |
| 6,712,836 | B1 | 3/2004 | Berg et al. |
| 6,716,207 | B2 | 4/2004 | Farnholtz |
| 6,729,356 | B1 | 5/2004 | Baker et al. |
| 6,730,118 | B2 | 5/2004 | Spenser et al. |
| 6,733,525 | B2 | 5/2004 | Yang et al. |
| 6,746,422 | B1 | 6/2004 | Noriega et al. |
| 6,749,560 | B1 | 6/2004 | Konstorum et al. |
| 6,767,362 | B2 | 7/2004 | Schreck |
| 6,780,200 | B2 | 8/2004 | Jansen |
| 6,790,229 | B1 | 9/2004 | Berreklouw |
| 6,790,230 | B2 | 9/2004 | Beyersdorf et al. |
| 6,830,584 | B1 | 12/2004 | Seguin |
| 6,875,231 | B2 | 4/2005 | Anduiza et al. |
| 6,893,460 | B2 | 5/2005 | Spenser et al. |
| 6,908,481 | B2 | 6/2005 | Cribier |
| 6,974,476 | B2 | 12/2005 | McGuckin et al. |
| 7,018,406 | B2 | 3/2006 | Seguin et al. |
| 7,186,265 | B2 | 3/2007 | Sharkawy et al. |
| 7,192,440 | B2 | 3/2007 | Andreas et al. |
| 7,198,646 | B2 | 4/2007 | Figulla et al. |
| 7,201,772 | B2 | 4/2007 | Schwammenthal et al. |
| 7,276,078 | B2 | 10/2007 | Spenser et al. |
| 7,276,084 | B2 | 10/2007 | Yang et al. |
| 7,318,278 | B2 | 1/2008 | Zhang et al. |
| 7,374,571 | B2 | 5/2008 | Pease et al. |
| 7,381,210 | B2 | 6/2008 | Zarbatany et al. |
| 7,381,219 | B2 | 6/2008 | Salahieh et al. |
| 7,393,360 | B2 | 7/2008 | Spenser et al. |
| 7,429,269 | B2 | 9/2008 | Schwammenthal et al. |
| 7,442,204 | B2 | 10/2008 | Schwammenthal et al. |
| 7,445,631 | B2 | 11/2008 | Salahieh et al. |
| 7,462,191 | B2 | 12/2008 | Spenser et al. |
| 7,510,575 | B2 | 3/2009 | Spenser et al. |
| 7,524,330 | B2 | 4/2009 | Berreklouw |
| 7,530,253 | B2 | 5/2009 | Spenser et al. |
| 7,553,324 | B2 | 6/2009 | Andreas et al. |
| 7,579,381 | B2 | 8/2009 | Dove |
| 7,585,321 | B2 | 9/2009 | Cribier |
| 7,618,446 | B2 | 11/2009 | Andersen et al. |
| 7,621,948 | B2 | 11/2009 | Herrmann et al. |
| 7,704,222 | B2 | 4/2010 | Wilk et al. |
| 7,736,327 | B2 | 6/2010 | Wilk et al. |
| 7,748,389 | B2 | 7/2010 | Salahieh et al. |
| 7,753,949 | B2 | 7/2010 | Lamphere et al. |
| 7,806,919 | B2 | 10/2010 | Bloom et al. |
| 7,824,443 | B2 | 11/2010 | Salahieh et al. |
| 7,837,727 | B2 | 11/2010 | Goetz et al. |
| 7,892,281 | B2 | 2/2011 | Seguin et al. |
| 7,914,569 | B2 | 3/2011 | Nguyen et al. |
| 7,914,575 | B2 | 3/2011 | Guyenot et al. |
| 7,959,672 | B2 | 6/2011 | Salahieh et al. |
| 7,972,378 | B2 | 7/2011 | Tabor et al. |
| 7,981,151 | B2 | 7/2011 | Rowe |
| 7,993,392 | B2 | 8/2011 | Righini et al. |
| 7,993,394 | B2 | 8/2011 | Hariton et al. |
| 8,007,992 | B2 | 8/2011 | Tian et al. |
| 8,016,877 | B2 | 9/2011 | Seguin et al. |
| 8,029,556 | B2 | 10/2011 | Rowe |
| 8,052,750 | B2 | 11/2011 | Tuval et al. |
| 8,070,800 | B2 | 12/2011 | Lock et al. |
| 8,070,802 | B2 | 12/2011 | Lamphere et al. |
| 8,075,615 | B2 | 12/2011 | Eberhardt et al. |
| 8,080,054 | B2 | 12/2011 | Rowe |
| 8,092,520 | B2 | 1/2012 | Quadri |
| 8,092,521 | B2 | 1/2012 | Figulla et al. |
| 8,109,996 | B2 | 2/2012 | Stacchino et al. |
| 8,118,866 | B2 | 2/2012 | Herrmann et al. |
| 8,136,218 | B2 | 3/2012 | Millwee et al. |
| 8,137,398 | B2 | 3/2012 | Tuval et al. |
| 8,157,852 | B2 | 4/2012 | Bloom et al. |
| 8,167,932 | B2 | 5/2012 | Bourang et al. |
| 8,167,934 | B2 | 5/2012 | Styrc et al. |
| 8,182,530 | B2 | 5/2012 | Huber |
| 8,206,437 | B2 | 6/2012 | Bonhoeffer et al. |
| 8,216,174 | B2 | 7/2012 | Wilk et al. |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,236,045 | B2 | 8/2012 | Benichou et al. |
| 8,246,675 | B2 | 8/2012 | Zegdi |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,287,584 | B2 | 10/2012 | Salahieh et al. |
| 8,313,525 | B2 | 11/2012 | Tuval et al. |
| 8,317,858 | B2 | 11/2012 | Straubinger et al. |
| 8,323,335 | B2 | 12/2012 | Rowe et al. |
| 8,337,541 | B2 | 12/2012 | Quadri et al. |
| 8,353,953 | B2 | 1/2013 | Giannetti et al. |
| 8,398,704 | B2 | 3/2013 | Straubinger et al. |
| 8,403,983 | B2 | 3/2013 | Quadri et al. |
| 8,414,644 | B2 | 4/2013 | Quadri et al. |
| 8,414,645 | B2 | 4/2013 | Dwork et al. |
| 8,416,643 | B2 | 4/2013 | Magee |
| 8,444,689 | B2 | 5/2013 | Zhang |
| 8,449,599 | B2 | 5/2013 | Chau et al. |
| 8,454,685 | B2 | 6/2013 | Hariton et al. |
| 8,460,368 | B2 | 6/2013 | Taylor et al. |
| 8,460,370 | B2 | 6/2013 | Zakay et al. |
| 8,470,023 | B2 | 6/2013 | Eidenschink et al. |
| 8,470,028 | B2 | 6/2013 | Thornton et al. |
| 8,475,521 | B2 | 7/2013 | Suri et al. |
| 8,475,523 | B2 | 7/2013 | Duffy |
| 8,479,380 | B2 | 7/2013 | Malewicz et al. |
| 8,491,650 | B2 | 7/2013 | Wiemeyer et al. |
| 8,500,733 | B2 | 8/2013 | Watson |
| 8,500,798 | B2 | 8/2013 | Rowe et al. |
| 8,511,244 | B2 | 8/2013 | Holecek et al. |
| 8,512,401 | B2 | 8/2013 | Murray et al. |
| 8,518,096 | B2 | 8/2013 | Nelson |
| 8,518,106 | B2 | 8/2013 | Duffy et al. |
| 8,562,663 | B2 | 10/2013 | Mearns et al. |
| 8,579,963 | B2 | 11/2013 | Tabor |
| 8,579,964 | B2 | 11/2013 | Lane et al. |
| 8,591,570 | B2 | 11/2013 | Revuelta et al. |
| 8,617,236 | B2 | 12/2013 | Paul et al. |
| 8,640,521 | B2 | 2/2014 | Righini et al. |
| 8,647,381 | B2 | 2/2014 | Essinger et al. |
| 8,652,145 | B2 | 2/2014 | Maimon et al. |
| 8,652,201 | B2 | 2/2014 | Oberti et al. |
| 8,652,202 | B2 | 2/2014 | Alon et al. |
| 8,652,203 | B2 | 2/2014 | Quadri et al. |
| 8,668,733 | B2 | 3/2014 | Haug et al. |
| 8,679,174 | B2 | 3/2014 | Ottma et al. |
| 8,679,404 | B2 | 3/2014 | Liburd et al. |

(56) References Cited

U.S. PATENT DOCUMENTS 8,685,086 B2 4/2014 Navia et al.
8,721,708 B2 5/2014 Sèguin et al.
8,721,714 B2 5/2014 Kelley
8,728,154 B2 5/2014 Alkhatib
8,728,155 B2 5/2014 Montorfano et al.
8,740,974 B2 6/2014 Lambrecht et al.
8,740,976 B2 6/2014 Tran et al.
8,747,458 B2 6/2014 Tuval et al.
8,747,459 B2 6/2014 Nguyen et al.
8,758,432 B2 6/2014 Solem
8,764,818 B2 7/2014 Gregg
8,771,344 B2 7/2014 Tran et al.
8,778,020 B2 7/2014 Gregg et al.
8,784,337 B2 7/2014 Voeller et al.
8,784,478 B2 7/2014 Tuval et al.
8,784,481 B2 7/2014 Alkhatib et al.
8,790,387 B2 7/2014 Nguyen et al.
8,795,357 B2 8/2014 Yohanan et al.
8,808,356 B2 8/2014 Braido et al.
8,828,078 B2 9/2014 Salahieh et al.
8,828,079 B2 9/2014 Thielen et al.
8,834,564 B2 9/2014 Tuval et al.
8,858,620 B2 10/2014 Salahieh et al.
8,870,948 B1 10/2014 Erzberger et al.
8,870,950 B2 10/2014 Hacohen
8,876,893 B2 11/2014 Dwork et al.
8,911,455 B2 12/2014 Quadri et al.
8,926,693 B2 1/2015 Duffy et al.
8,926,694 B2 1/2015 Costello
8,939,960 B2 1/2015 Rosenman et al.
8,945,209 B2 2/2015 Bonyuet et al.
8,961,593 B2 2/2015 Bonhoeffer et al.
8,961,595 B2 2/2015 Alkhatib
8,974,524 B2 3/2015 Yeung et al.
8,979,922 B2 3/2015 Jayasinghe et al.
8,986,375 B2 3/2015 Garde et al.
8,998,980 B2 4/2015 Shipley et al.
9,005,273 B2 4/2015 Salahieh et al.
9,011,521 B2 4/2015 Haug et al.
9,011,523 B2 4/2015 Seguin
9,011,524 B2 4/2015 Eberhardt
9,028,545 B2 5/2015 Taylor
9,034,032 B2 5/2015 McLean et al.
9,055,937 B2 6/2015 Rowe et al.
9,066,801 B2 6/2015 Kovalsky et al.
9,078,749 B2 7/2015 Lutter et al.
9,078,751 B2 7/2015 Naor
9,125,738 B2 9/2015 Figulla et al.
9,173,737 B2 11/2015 Hill et al.
9,180,004 B2 11/2015 Alkhatib
9,186,249 B2 11/2015 Rolando et al.
9,277,990 B2 3/2016 Klima et al.
9,277,993 B2 3/2016 Gamarra et al.
9,289,291 B2 3/2016 Gorman et al.
9,295,551 B2 3/2016 Straubinger et al.
9,445,897 B2 9/2016 Bishop et al.
9,456,877 B2 10/2016 Weitzner et al.
9,681,968 B2 6/2017 Goetz et al.
9,687,345 B2 6/2017 Rabito et al.
9,693,863 B2 7/2017 Nelson et al.
9,700,329 B2 7/2017 Metzger et al.
9,700,411 B2 7/2017 Klima et al.
9,724,083 B2 8/2017 Quadri et al.
9,730,790 B2 8/2017 Quadri et al.
9,730,791 B2 8/2017 Ratz et al.
9,795,479 B2 10/2017 Lim et al.
9,833,313 B2 12/2017 Board et al.
9,861,473 B2 1/2018 Lafontaine
9,861,476 B2 1/2018 Salahieh et al.
9,861,477 B2 1/2018 Backus et al.
9,867,698 B2 1/2018 Kovalsky et al.
9,877,830 B2 1/2018 Lim et al.
9,889,029 B2 2/2018 Li et al.
9,895,225 B2 2/2018 Rolando et al.
9,925,045 B2 3/2018 Creaven et al.
10,004,599 B2 6/2018 Rabito et al.
10,117,744 B2 11/2018 Ratz et al.
10,179,044 B2 1/2019 Ratz et al.
10,219,897 B2 3/2019 Essinger et al.
10,350,065 B2 7/2019 Quadri
10,350,066 B2 7/2019 Cooper et al.
10,376,363 B2 8/2019 Quadri et al.
10,555,809 B2 2/2020 Hastings et al.
10,575,951 B2 3/2020 Johnson et al.
10,583,000 B2 3/2020 Ratz et al.
10,639,146 B2 5/2020 Quadri et al.
10,695,177 B2 6/2020 Hariton et al.
10,758,344 B2 9/2020 Hariton et al.
11,406,499 B2 8/2022 Zhang et al.
11,452,598 B2 9/2022 Essinger et al.
11,672,658 B2 6/2023 Hariton et al.
11,701,225 B2 7/2023 Hammer et al.
11,903,829 B1 2/2024 Ma et al.
2001/0021872 A1 9/2001 Bailey et al.
2002/0032481 A1 3/2002 Gabbay
2002/0045929 A1 4/2002 Diaz
2002/0052644 A1 5/2002 Shaolian et al.
2002/0107565 A1 8/2002 Greenhalgh
2002/0123802 A1 9/2002 Snyders
2002/0173842 A1 11/2002 Buchanan
2003/0050694 A1 3/2003 Yang et al.
2003/0055495 A1 3/2003 Pease et al.
2003/0100939 A1 5/2003 Yodfat et al.
2003/0105517 A1 6/2003 White et al.
2003/0120333 A1 6/2003 Ouriel et al.
2003/0130729 A1 7/2003 Paniagua et al.
2003/0149477 A1 8/2003 Gabbay
2003/0149478 A1 8/2003 Figulla et al.
2003/0158597 A1 8/2003 Quiachon et al.
2003/0176914 A1 9/2003 Rabkin et al.
2003/0199971 A1 10/2003 Tower et al.
2003/0212454 A1 11/2003 Scott et al.
2003/0220683 A1 11/2003 Minasian et al.
2004/0039436 A1 2/2004 Spenser et al.
2004/0092858 A1 5/2004 Wilson et al.
2004/0093075 A1 5/2004 Kuehne
2004/0117009 A1 6/2004 Cali et al.
2004/0133263 A1 7/2004 Dusbabek et al.
2004/0133273 A1 7/2004 Cox
2004/0138734 A1 7/2004 Chobotov et al.
2004/0186563 A1 9/2004 Lobbi
2004/0186565 A1 9/2004 Schreck
2004/0210307 A1 10/2004 Khairkhahan
2004/0215325 A1 10/2004 Penn et al.
2004/0225353 A1 11/2004 McGuckin et al.
2004/0236411 A1 11/2004 Sarac et al.
2004/0260389 A1 12/2004 Case et al.
2005/0033398 A1 2/2005 Seguin
2005/0075727 A1 4/2005 Wheatley
2005/0090887 A1 4/2005 Pryor
2005/0096738 A1 5/2005 Cali et al.
2005/0107872 A1 5/2005 Mensah et al.
2005/0137682 A1 6/2005 Justino
2005/0137686 A1 6/2005 Salahieh et al.
2005/0137687 A1 6/2005 Salahieh et al.
2005/0137688 A1 6/2005 Salahieh et al.
2005/0137691 A1 6/2005 Salahieh et al.
2005/0137698 A1 6/2005 Salahieh et al.
2005/0159811 A1 7/2005 Lane
2005/0182486 A1 8/2005 Gabbay
2005/0203614 A1 9/2005 Forster et al.
2005/0203617 A1 9/2005 Forster et al.
2005/0216079 A1 9/2005 MaCoviak
2005/0234546 A1 10/2005 Nugent et al.
2005/0288766 A1 12/2005 Plain et al.
2006/0020327 A1 1/2006 Lashinski et al.
2006/0025857 A1 2/2006 Bergheim et al.
2006/0058872 A1 3/2006 Salahieh et al.
2006/0095115 A1 5/2006 Bladillah et al.
2006/0095119 A1 5/2006 Bolduc
2006/0142837 A1 6/2006 Haverkost et al.
2006/0149350 A1 7/2006 Patel et al.
2006/0161249 A1 7/2006 Realyvasquez et al.
2006/0173537 A1 8/2006 Yang et al.

(56) References Cited

U.S. PATENT DOCUMENTS

| | | | |
|---|---|---|---|
| 2006/0195134 | A1 | 8/2006 | Crittenden |
| 2006/0195183 | A1 | 8/2006 | Navia et al. |
| 2006/0212110 | A1 | 9/2006 | Osborne et al. |
| 2006/0229719 | A1 | 10/2006 | Marquez et al. |
| 2006/0241745 | A1 | 10/2006 | Solem |
| 2006/0259135 | A1 | 11/2006 | Navia et al. |
| 2006/0259137 | A1 | 11/2006 | Artof et al. |
| 2006/0276874 | A1 | 12/2006 | Wilson et al. |
| 2006/0293745 | A1 | 12/2006 | Carpentier et al. |
| 2007/0005131 | A1 | 1/2007 | Taylor |
| 2007/0010877 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0050021 | A1 | 3/2007 | Johnson |
| 2007/0066863 | A1 | 3/2007 | Rafiee et al. |
| 2007/0088431 | A1 | 4/2007 | Bourang et al. |
| 2007/0100432 | A1 | 5/2007 | Case et al. |
| 2007/0100439 | A1 | 5/2007 | Cangialosi et al. |
| 2007/0112422 | A1 | 5/2007 | Dehdashtian |
| 2007/0129794 | A1 | 6/2007 | Realyvasquez |
| 2007/0142906 | A1 | 6/2007 | Figulla et al. |
| 2007/0156224 | A1 | 7/2007 | Cioanta et al. |
| 2007/0203503 | A1 | 8/2007 | Salahieh et al. |
| 2007/0203575 | A1 | 8/2007 | Forster et al. |
| 2007/0213813 | A1 | 9/2007 | Von Segesser et al. |
| 2007/0255394 | A1 | 11/2007 | Ryan |
| 2007/0270943 | A1 | 11/2007 | Solem et al. |
| 2008/0021546 | A1 | 1/2008 | Patz et al. |
| 2008/0065011 | A1 | 3/2008 | Marchand et al. |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0082164 | A1 | 4/2008 | Friedman |
| 2008/0082165 | A1 | 4/2008 | Wilson et al. |
| 2008/0082166 | A1 | 4/2008 | Styrc et al. |
| 2008/0097581 | A1 | 4/2008 | Shanley |
| 2008/0114442 | A1 | 5/2008 | Mitchell et al. |
| 2008/0125853 | A1 | 5/2008 | Bailey et al. |
| 2008/0147179 | A1 | 6/2008 | Cai et al. |
| 2008/0147183 | A1 | 6/2008 | Styrc |
| 2008/0154355 | A1 | 6/2008 | Benichou et al. |
| 2008/0161910 | A1 | 7/2008 | Revuelta et al. |
| 2008/0177381 | A1 | 7/2008 | Navia et al. |
| 2008/0183273 | A1 | 7/2008 | Mesana et al. |
| 2008/0208328 | A1 | 8/2008 | Antocci et al. |
| 2008/0208332 | A1 | 8/2008 | Lamphere et al. |
| 2008/0221672 | A1 | 9/2008 | Lamphere et al. |
| 2008/0228254 | A1 | 9/2008 | Ryan |
| 2008/0255660 | A1 | 10/2008 | Guyenot et al. |
| 2008/0255661 | A1 | 10/2008 | Straubinger et al. |
| 2008/0281411 | A1 | 11/2008 | Berreklouw |
| 2009/0005863 | A1 | 1/2009 | Goetz et al. |
| 2009/0054968 | A1 | 2/2009 | Bonhoeffer et al. |
| 2009/0054974 | A1 | 2/2009 | McGuckin et al. |
| 2009/0076598 | A1 | 3/2009 | Salahieh et al. |
| 2009/0112309 | A1 | 4/2009 | Jaramillo et al. |
| 2009/0138079 | A1 | 5/2009 | Tuval et al. |
| 2009/0157175 | A1 | 6/2009 | Benichou |
| 2009/0164005 | A1 | 6/2009 | Dove et al. |
| 2009/0171432 | A1 | 7/2009 | Von Segesser et al. |
| 2009/0171447 | A1 | 7/2009 | Von Segesser et al. |
| 2009/0171456 | A1 | 7/2009 | Kveen et al. |
| 2009/0182413 | A1 | 7/2009 | Burkart et al. |
| 2009/0188964 | A1 | 7/2009 | Orlov |
| 2009/0216310 | A1 | 8/2009 | Straubinger et al. |
| 2009/0216313 | A1 | 8/2009 | Straubinger et al. |
| 2009/0216322 | A1 | 8/2009 | Le et al. |
| 2009/0222076 | A1 | 9/2009 | Figulla et al. |
| 2009/0234443 | A1 | 9/2009 | Ottma et al. |
| 2009/0240320 | A1 | 9/2009 | Tuval et al. |
| 2009/0270972 | A1 | 10/2009 | Lane |
| 2009/0276027 | A1 | 11/2009 | Glynn |
| 2009/0276040 | A1 | 11/2009 | Rowe et al. |
| 2009/0281618 | A1 | 11/2009 | Hill et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0292350 | A1 | 11/2009 | Eberhardt et al. |
| 2009/0306768 | A1 | 12/2009 | Quadri |
| 2009/0319037 | A1 | 12/2009 | Rowe et al. |
| 2010/0016958 | A1 | 1/2010 | St. Goar et al. |
| 2010/0024818 | A1 | 2/2010 | Stenzler et al. |
| 2010/0042208 | A1 | 2/2010 | Herrmann et al. |
| 2010/0049313 | A1 | 2/2010 | Alon et al. |
| 2010/0069852 | A1 | 3/2010 | Kelley |
| 2010/0114305 | A1 | 5/2010 | Kang et al. |
| 2010/0131054 | A1 | 5/2010 | Tuval et al. |
| 2010/0137979 | A1 | 6/2010 | Tuval et al. |
| 2010/0145438 | A1 | 6/2010 | Barone |
| 2010/0174362 | A1 | 7/2010 | Straubinger et al. |
| 2010/0191326 | A1 | 7/2010 | Alkhatib |
| 2010/0204781 | A1 | 8/2010 | Alkhatib |
| 2010/0217382 | A1 | 8/2010 | Chau et al. |
| 2010/0249894 | A1 | 9/2010 | Oba et al. |
| 2010/0249911 | A1 | 9/2010 | Alkhatib |
| 2010/0256723 | A1 | 10/2010 | Murray |
| 2010/0262231 | A1 | 10/2010 | Tuval et al. |
| 2010/0305685 | A1 | 12/2010 | Millwee et al. |
| 2010/0312333 | A1 | 12/2010 | Navia et al. |
| 2011/0015616 | A1 | 1/2011 | Straubinger et al. |
| 2011/0015729 | A1 | 1/2011 | Jimenez et al. |
| 2011/0029072 | A1 | 2/2011 | Gabbay |
| 2011/0098805 | A1 | 4/2011 | Dwork et al. |
| 2011/0137397 | A1 | 6/2011 | Chau et al. |
| 2011/0178597 | A9 | 7/2011 | Navia et al. |
| 2011/0208290 | A1 | 8/2011 | Straubinger et al. |
| 2011/0208297 | A1 | 8/2011 | Tuval et al. |
| 2011/0208298 | A1 | 8/2011 | Tuval et al. |
| 2011/0224785 | A1 | 9/2011 | Hacohen |
| 2011/0238159 | A1 | 9/2011 | Guyenot et al. |
| 2011/0251681 | A1 | 10/2011 | Shipley et al. |
| 2011/0264196 | A1 | 10/2011 | Savage et al. |
| 2011/0264198 | A1 | 10/2011 | Murray et al. |
| 2011/0288634 | A1 | 11/2011 | Tuval et al. |
| 2011/0313515 | A1 | 12/2011 | Quadri et al. |
| 2011/0319989 | A1 | 12/2011 | Lane et al. |
| 2012/0022639 | A1 | 1/2012 | Hacohen et al. |
| 2012/0035722 | A1 | 2/2012 | Tuval |
| 2012/0041550 | A1 | 2/2012 | Salahieh et al. |
| 2012/0046741 | A1 | 2/2012 | Tuval et al. |
| 2012/0046742 | A1 | 2/2012 | Tuval et al. |
| 2012/0078360 | A1 | 3/2012 | Rafiee |
| 2012/0101570 | A1 | 4/2012 | Tuval et al. |
| 2012/0101571 | A1 | 4/2012 | Thambar et al. |
| 2012/0101572 | A1 | 4/2012 | Kovalsky et al. |
| 2012/0123529 | A1 | 5/2012 | Levi et al. |
| 2012/0185039 | A1 | 7/2012 | Tuval et al. |
| 2012/0197386 | A1 | 8/2012 | Von Segesser et al. |
| 2012/0209374 | A1 | 8/2012 | Bonhoeffer et al. |
| 2012/0215303 | A1 | 8/2012 | Quadri et al. |
| 2012/0271398 | A1 | 10/2012 | Essinger et al. |
| 2012/0283823 | A1 | 11/2012 | Bonhoeffer et al. |
| 2012/0290062 | A1 | 11/2012 | McNamara et al. |
| 2012/0296418 | A1 | 11/2012 | Bonyuet et al. |
| 2012/0310328 | A1 | 12/2012 | Olson et al. |
| 2012/0310336 | A1 | 12/2012 | Figulla et al. |
| 2013/0006294 | A1 | 1/2013 | Kashkarov et al. |
| 2013/0035759 | A1 | 2/2013 | Gross et al. |
| 2013/0073035 | A1 | 3/2013 | Tuval et al. |
| 2013/0079869 | A1 | 3/2013 | Straubinger et al. |
| 2013/0172992 | A1 | 7/2013 | Gross et al. |
| 2013/0190861 | A1 | 7/2013 | Chau et al. |
| 2013/0190862 | A1 | 7/2013 | Pintor et al. |
| 2013/0197622 | A1 | 8/2013 | Mitra et al. |
| 2013/0211508 | A1 | 8/2013 | Lane et al. |
| 2013/0253635 | A1 | 9/2013 | Straubinger et al. |
| 2013/0253642 | A1 | 9/2013 | Brecker |
| 2013/0310928 | A1 | 11/2013 | Morriss et al. |
| 2013/0331929 | A1 | 12/2013 | Mitra et al. |
| 2013/0338766 | A1 | 12/2013 | Hastings et al. |
| 2013/0345786 | A1 | 12/2013 | Behan |

(56) References Cited

U.S. PATENT DOCUMENTS

2014/0018912 A1 1/2014 Delaloye et al.
2014/0025163 A1 1/2014 Padala et al.
2014/0039611 A1 2/2014 Lane et al.
2014/0052237 A1 2/2014 Lane et al.
2014/0100651 A1 4/2014 Kheradvar et al.
2014/0163668 A1 6/2014 Rafiee
2014/0172077 A1 6/2014 Bruchman et al.
2014/0172083 A1 6/2014 Bruchman et al.
2014/0194981 A1 7/2014 Menk et al.
2014/0207231 A1 7/2014 Hacohen et al.
2014/0214157 A1 7/2014 Börtlein et al.
2014/0222136 A1 8/2014 Geist et al.
2014/0222139 A1 8/2014 Nguyen et al.
2014/0222142 A1 8/2014 Kovalsky et al.
2014/0222144 A1 8/2014 Eberhardt et al.
2014/0243966 A1 8/2014 Garde et al.
2014/0257467 A1 9/2014 Lane et al.
2014/0277390 A1 9/2014 Ratz et al.
2014/0277403 A1 9/2014 Peter
2014/0277412 A1 9/2014 Börtlein et al.
2014/0277422 A1 9/2014 Ratz et al.
2014/0277426 A1 9/2014 Dakin et al.
2014/0277427 A1 9/2014 Ratz et al.
2014/0296973 A1 10/2014 Bergheim et al.
2014/0296975 A1 10/2014 Tegels et al.
2014/0303719 A1 10/2014 Cox et al.
2014/0309728 A1 10/2014 Dehdashtian et al.
2014/0324160 A1 10/2014 Benichou et al.
2014/0324164 A1 10/2014 Gross et al.
2014/0330368 A1 11/2014 Gloss et al.
2014/0330371 A1 11/2014 Gloss et al.
2014/0330372 A1 11/2014 Weston et al.
2014/0336754 A1 11/2014 Gurskis et al.
2014/0343669 A1 11/2014 Lane et al.
2014/0343670 A1 11/2014 Bakis et al.
2014/0350666 A1 11/2014 Righini
2014/0350668 A1 11/2014 Delaloye et al.
2014/0358223 A1 12/2014 Rafiee et al.
2014/0364939 A1 12/2014 Deshmukh et al.
2014/0364943 A1 12/2014 Conklin
2014/0371842 A1 12/2014 Marquez et al.
2014/0371844 A1 12/2014 Dale et al.
2014/0371847 A1 12/2014 Madrid et al.
2014/0371848 A1 12/2014 Murray et al.
2015/0005863 A1 1/2015 Para
2015/0018944 A1 1/2015 O'Connell et al.
2015/0039083 A1 2/2015 Rafiee
2015/0142100 A1 5/2015 Morriss et al.
2015/0142103 A1 5/2015 Vidlund
2015/0148731 A1 5/2015 McNamara et al.
2015/0173897 A1 6/2015 Raanani et al.
2015/0196390 A1 7/2015 Ma et al.
2015/0209141 A1 7/2015 Braido et al.
2015/0272737 A1 10/2015 Dale et al.
2015/0297346 A1 10/2015 Duffy et al.
2015/0335429 A1 11/2015 Morriss et al.
2015/0351903 A1 12/2015 Morriss et al.
2015/0359629 A1 12/2015 Ganesan et al.
2016/0000591 A1 1/2016 Lei et al.
2016/0030169 A1 2/2016 Shahriari
2016/0030170 A1 2/2016 Alkhatib et al.
2016/0030171 A1 2/2016 Quijano et al.
2016/0038280 A1 2/2016 Morriss et al.
2016/0038281 A1 2/2016 Delaloye et al.
2016/0074160 A1 3/2016 Christianson et al.
2016/0106537 A1 4/2016 Christianson et al.
2016/0113765 A1 4/2016 Ganesan et al.
2016/0113768 A1 4/2016 Ganesan et al.
2016/0143732 A1 5/2016 Glimsdale
2016/0158010 A1 6/2016 Lim et al.
2016/0166383 A1 6/2016 Lim et al.
2016/0184097 A1 6/2016 Lim et al.
2016/0199206 A1 7/2016 Lim et al.
2016/0213473 A1 7/2016 Hacohen et al.
2016/0235529 A1 8/2016 Ma et al.
2016/0278923 A1 9/2016 Krans et al.
2016/0279386 A1 9/2016 Dale et al.
2016/0310267 A1 10/2016 Zeng et al.
2016/0367368 A1* 12/2016 Vidlund ................ A61B 90/06
2017/0042678 A1 2/2017 Ganesan et al.
2017/0079785 A1 3/2017 Li
2017/0128209 A1 5/2017 Morriss et al.
2017/0216023 A1 8/2017 Lane et al.
2017/0216575 A1 8/2017 Asleson et al.
2017/0257902 A1 9/2017 Xing et al.
2017/0258614 A1 9/2017 Griffin
2017/0325945 A1 11/2017 Dale et al.
2017/0325954 A1 11/2017 Perszyk
2017/0333186 A1 11/2017 Spargias
2017/0348096 A1 12/2017 Anderson
2017/0367821 A1 12/2017 Landon et al.
2017/0367823 A1 12/2017 Hariton et al.
2018/0014931 A1 1/2018 Morriss et al.
2018/0021129 A1 1/2018 Peterson et al.
2018/0055629 A1 3/2018 Oba et al.
2018/0055636 A1 3/2018 Valencia et al.
2018/0085218 A1 3/2018 Eidenschink
2018/0110534 A1 4/2018 Gavala et al.
2018/0110622 A1 4/2018 Gregg et al.
2018/0116790 A1 5/2018 Ratz et al.
2018/0126119 A1 5/2018 McNiven et al.
2018/0296341 A1 10/2018 Noe et al.
2018/0344457 A1 12/2018 Gross et al.
2018/0344490 A1 12/2018 Fox et al.
2019/0008639 A1 1/2019 Landon et al.
2019/0008640 A1 1/2019 Cooper et al.
2019/0060072 A1 2/2019 Zeng
2019/0262129 A1 8/2019 Cooper et al.
2020/0000579 A1 1/2020 Manash et al.
2020/0108225 A1 4/2020 Jamal et al.
2020/0138572 A1 5/2020 Zhao et al.
2020/0323668 A1 10/2020 Diedering et al.
2020/0345494 A1 11/2020 Srinimukesh et al.
2020/0352718 A1 11/2020 Rowe et al.
2021/0015615 A1 1/2021 Groothuis et al.
2021/0145576 A1 5/2021 Becerra et al.
2021/0228354 A1 7/2021 Rafiee et al.
2021/0259835 A1 8/2021 Tyler, II et al.
2021/0307900 A1 10/2021 Hacohen
2021/0378817 A1 12/2021 Nia et al.
2021/0386544 A1 12/2021 Cooper et al.
2022/0142777 A1 5/2022 Scheinblum et al.
2022/0287836 A1 9/2022 Landon et al.
2022/0346993 A1 11/2022 Srinimukesh et al.
2023/0000624 A1 1/2023 Okabe et al.
2023/0200980 A1 6/2023 Peterson et al.
2023/0218391 A1 7/2023 Dass et al.
2023/0380963 A1 11/2023 Kaufman et al.
2023/0390052 A1 12/2023 Okafor et al.
2023/0404753 A1 12/2023 Luong et al.
2024/0008978 A1 1/2024 Nawalakhe et al.
2024/0091000 A1 3/2024 King et al.

FOREIGN PATENT DOCUMENTS

CN 101460102 A 6/2009
CN 103124537 A 5/2013
DE 2246526 A1 3/1973
DE 19532846 A1 3/1997
DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
DE 10010074 B4 4/2005
DE 102006052564 B3 12/2007
EP 0144167 A2 6/1985
EP 0103546 B1 5/1988
EP 0592410 B1 10/1995
EP 0850607 A1 7/1998
EP 0597967 B1 12/1999
EP 1057460 A1 12/2000

(56) References Cited

FOREIGN PATENT DOCUMENTS

| | | | |
|---|---|---|---|
| EP | 1088529 | A2 | 4/2001 |
| EP | 1469797 | A1 | 10/2004 |
| EP | 1259194 | B1 | 2/2005 |
| EP | 1171059 | B1 | 11/2005 |
| EP | 1255510 | B1 | 4/2007 |
| EP | 1239901 | B1 | 10/2007 |
| EP | 1849440 | A1 | 10/2007 |
| EP | 1570809 | B1 | 1/2009 |
| EP | 1472996 | B1 | 9/2009 |
| EP | 1653888 | B1 | 9/2009 |
| EP | 1935377 | B1 | 3/2010 |
| EP | 1369098 | B1 | 4/2014 |
| EP | 2124826 | B1 | 7/2014 |
| EP | 2745805 | B1 | 6/2015 |
| EP | 2749254 | B1 | 6/2015 |
| EP | 2918249 | A2 | 9/2015 |
| EP | 2168536 | B1 | 4/2016 |
| EP | 2413842 | B1 | 8/2017 |
| EP | 2446915 | B1 | 1/2018 |
| EP | 3057541 | B1 | 1/2018 |
| EP | 3037064 | B1 | 3/2018 |
| EP | 3046511 | B1 | 3/2018 |
| EP | 3142603 | B1 | 3/2018 |
| EP | 3075354 | B1 | 11/2018 |
| EP | 3184083 | B1 | 2/2019 |
| EP | 2918249 | B1 | 4/2020 |
| EP | 3417813 | B1 | 5/2020 |
| EP | 2777616 | B1 | 8/2020 |
| EP | 3139864 | B1 | 11/2020 |
| EP | 2750630 | B1 | 6/2021 |
| EP | 2777617 | B1 | 9/2022 |
| EP | 2948103 | B1 | 12/2022 |
| EP | 2967858 | B1 | 1/2023 |
| EP | 3570779 | B1 | 2/2023 |
| EP | 3294220 | B1 | 12/2023 |
| FR | 2788217 | A1 | 7/2000 |
| GB | 1264471 | A | 2/1972 |
| GB | 1315844 | A | 5/1973 |
| GB | 2056023 | A | 3/1981 |
| GB | 2398245 | A | 8/2004 |
| JP | S5227469 | B1 | 7/1977 |
| JP | H08503634 | A | 4/1996 |
| JP | 2000500047 | A | 1/2000 |
| JP | 2003509087 | A | 3/2003 |
| JP | 2006528034 | A | 12/2006 |
| JP | 2007083089 | A | 4/2007 |
| JP | 4236010 | B2 | 3/2009 |
| JP | 4307744 | B2 | 8/2009 |
| JP | 2010518978 | A | 6/2010 |
| JP | 2011500286 | A | 1/2011 |
| JP | 5253504 | B2 | 7/2013 |
| SU | 1271508 | A1 | 11/1986 |
| WO | 1991016041 | A1 | 10/1991 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2000061034 | A1 | 10/2000 |
| WO | 2001028459 | A1 | 4/2001 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002036048 | A1 | 5/2002 |
| WO | WO-2002041789 | A2 | 5/2002 |
| WO | 2003047468 | A1 | 6/2003 |
| WO | 2003092554 | A1 | 11/2003 |
| WO | 2004030569 | A2 | 4/2004 |
| WO | 2005011534 | A1 | 2/2005 |
| WO | 2005034812 | A1 | 4/2005 |
| WO | WO-2005062980 | A2 | 7/2005 |
| WO | 2005087140 | A1 | 9/2005 |
| WO | 2005102015 | A2 | 11/2005 |
| WO | 2006014233 | A2 | 2/2006 |
| WO | 2006034008 | A2 | 3/2006 |
| WO | 2006085225 | A1 | 8/2006 |
| WO | 2006108090 | A2 | 10/2006 |
| WO | 2006111391 | A1 | 10/2006 |
| WO | 2006138173 | A2 | 12/2006 |
| WO | 2007025028 | A1 | 3/2007 |
| WO | 2008005405 | A2 | 1/2008 |
| WO | 2008035337 | A2 | 3/2008 |
| WO | 2008125153 | A1 | 10/2008 |
| WO | 2008147964 | A1 | 12/2008 |
| WO | 2008150529 | A1 | 12/2008 |
| WO | 2009024859 | A2 | 2/2009 |
| WO | 2009026563 | A2 | 2/2009 |
| WO | 2009042196 | A2 | 4/2009 |
| WO | 2009091509 | A1 | 7/2009 |
| WO | 2009094500 | A1 | 7/2009 |
| WO | 2010005524 | A2 | 1/2010 |
| WO | 2010008549 | A1 | 1/2010 |
| WO | 2010121076 | A2 | 10/2010 |
| WO | 2011002996 | A2 | 1/2011 |
| WO | 2011081997 | A1 | 7/2011 |
| WO | 2012032187 | A1 | 3/2012 |
| WO | 2012095455 | A2 | 7/2012 |
| WO | WO-2012158837 | A1 | 11/2012 |
| WO | 2013028387 | A2 | 2/2013 |
| WO | 2013106585 | A1 | 7/2013 |
| WO | 2014018432 | A2 | 1/2014 |
| WO | 2014079291 | A1 | 5/2014 |
| WO | 2014145338 | A1 | 9/2014 |
| WO | 2014149865 | A1 | 9/2014 |
| WO | 2014163706 | A1 | 10/2014 |
| WO | 2014194178 | A1 | 12/2014 |
| WO | 2015057407 | A1 | 4/2015 |
| WO | 2015077274 | A1 | 5/2015 |
| WO | 2016016899 | A1 | 2/2016 |
| WO | 2017035487 | A1 | 3/2017 |
| WO | 2018213209 | A1 | 11/2018 |
| WO | 2022002054 | A1 | 1/2022 |
| WO | 2023006048 | A1 | 2/2023 |
| WO | 2023076103 | A1 | 5/2023 |
| WO | 2023081236 | A1 | 5/2023 |
| WO | 2023091769 | A1 | 5/2023 |
| WO | 2023096804 | A1 | 6/2023 |
| WO | 2023154250 | A1 | 8/2023 |
| WO | 2023196150 | A1 | 10/2023 |
| WO | 2023244454 | A1 | 12/2023 |
| WO | 2023244767 | A1 | 12/2023 |
| WO | 2023250114 | A1 | 12/2023 |
| WO | 2024001789 | A1 | 1/2024 |
| WO | 2024003620 | A1 | 1/2024 |
| WO | 2024007575 | A1 | 1/2024 |
| WO | 2024009540 | A1 | 1/2024 |
| WO | 2024010739 | A1 | 1/2024 |
| WO | 2024030520 | A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

(56) References Cited

OTHER PUBLICATIONS

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob&Smith's Operative Surgery, Fourth Edition, pp. 415-424, Butterworths 1986.
Bavaria, Joseph E. M.D et al.: "Transcatheter Mitral Valve Implantation: The Future Gold Standard for MR?".
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31.
Feldman, Ted, MD. "Prospects for Percutaneous Valve Therapies," Circulation 2007;116:2866-2877.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.
Lutter, Georg, et al., "Off-Pump Transapical Mitral Valve Replacement," European Journal of Cardio-thoracic Surgery 36 (2009) 124-128.
Ma, Liang, et al., "'Double-Crowned Valved Stents For Off-Pump Mitral Valve Replacement," European Journal of Cardio-thoracic Surgery 28 (2005) 194-199.
Mack, Michael, M.D., "Antegrade Transcatheter Mitral valve Implantation: A Short-term Experience in Swine Model,".
Mack, Michael, M.D., "Antegrade Transcatheter Mitral valve Implantation: On-Going Experience in Swine Model,".
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184.
Quadri, Arshad M.D., "Transcatheter Mitral Valve Implantation (TMVI) (An Acute In Vivo Study),".
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies,".
Spillner, J. et al., "New Sutureless 'Atrial- Mitral-Valve Prosthesis' For Minimally Invasive Mitral Valve Therapy," Textile Research Journal, 2010, in 7 pages.
Sondergaard, Lars, et al., "Transcatheter Mitral Valve Implantation: CardiAQ ™," TCT 2013.
Sondergaard, Lars, et al., "Transcatheter Mitral Valve Implantation: CardiAQ™," EuroPCR 2013.
Sondergaard, Lars, "CardiAQ TMVR FIH—Generation 2," TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"CardiAQ Valve Technologies, Percutaneous Mitral Valve Replacement, Company Overview," at TVT on Jun. 25, 2009.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.
Herrmann, Howard C., M.D., "Advances in Transseptal Transcatheter Mitral Valve Replacement," Cardiovascular Research Foundation, tct, Sep. 21-25, 2018, 10 Pages, San Diego, California.
Neale, Todd, "Flushing TAVI Valves With Carbon Dioxide May Protect Against Brain Injury", News Conference News, EuroPCR 2023, TCTMD, May 16, 2023, Paris France.
Transcatheter Aortic Valve Delivery Catheter System Compression Loading System, Medtronic CoreValveSystem, Medtronic Inc, 2014, 61 pages, Santa Ana, California.

* cited by examiner

INVERSION DELIVERY DEVICE AND METHOD FOR A PROSTHESIS

BACKGROUND OF THE INVENTION

This application is a continuation of U.S. patent application Ser. No. 16/384,707 filed Apr. 15, 2019 entitled Inversion Delivery Device And Method For A Prosthesis, which is a continuation of U.S. patent application Ser. No. 15/370,009 filed Dec. 6, 2016 entitled Inversion Delivery Device And Method For A Prosthesis, which is a divisional of U.S. patent application Ser. No. 14/270,286 filed on May 5, 2014 entitled Inversion Delivery Device And Method For A Prosthesis (now U.S. Pat. No. 9,693,863 issued Jul. 4, 2017), and is a divisional of U.S. patent application Ser. No. 14/270,300 filed on May 5, 2014 entitled Inversion Delivery Device And Method For A Prosthesis (now U.S. Pat. No. 9,795,478 issued Oct. 24, 2017), both of which (Ser. Nos. 14/270,286 and 14/270,300) are continuations of U.S. patent application Ser. No. 13/657,800 filed Oct. 22, 2012 entitled Inversion Delivery Device And Method For A Prosthesis (now U.S. Pat. No. 9,522,064 issued Dec. 20, 2016), which is a Continuation-In-Part of U.S. patent application Ser. No. 13/473,475, filed on May 16, 2012 entitled Inversion Delivery Device And Method For A Prosthesis, which claims priority to U.S. Provisional Application Ser. No. 61/486,682 filed May 16, 2011 entitled Inversion Delivery Device And Method For A Prosthesis, all of which are hereby incorporated herein by reference in their entireties.

BACKGROUND OF THE INVENTION

There has been a significant movement toward developing and performing cardiovascular surgeries using a percutaneous approach. Through the use of one or more catheters that are introduced through, for example, the femoral artery, tools and devices can be delivered to a desired area in the cardiovascular system to perform many number of complicated procedures that normally otherwise require an invasive surgical procedure. Such approaches greatly reduce the trauma endured by the patient and can significantly reduce recovery periods. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of heart valve leaflets. Such immobility also may lead to a narrowing, or stenosis, of the passageway through the valve. The increased resistance to blood flow that a stenosed valve presents can eventually lead to heart failure and ultimately death.

Treating valve stenosis or regurgitation has heretofore involved complete removal of the existing native valve through an open-heart procedure followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Historically, such valve replacement surgery has been performed using traditional open-heart surgery where the chest is opened, the heart stopped, the patient placed on cardiopulmonary bypass, the native valve excised and the replacement valve attached. A proposed percutaneous valve replacement alternative method on the other hand, is disclosed in U.S. Pat. No. 6,168,614 (the entire contents of which are hereby incorporated by reference) issued to Andersen et al. In this patent, the prosthetic valve is mounted on a stent that is collapsed to a size that fits within a catheter. The catheter is then inserted into the patient's vasculature and moved so as to position the collapsed stent at the location of the native valve. A deployment mechanism is activated that expands the stent containing the replacement valve against the valve cusps. The expanded structure includes a stent configured to have a valve shape with valve leaflet supports begins to take on the function of the native valve. As a result, a full valve replacement has been achieved but at a significantly reduced physical impact to the patient.

However, this approach has decided shortcomings. One particular drawback with the percutaneous approach disclosed in the Andersen '614 patent is the difficulty in preventing leakage around the perimeter of the new valve after implantation. Since the tissue of the native valve remains within the lumen, there is a strong likelihood that the commissural junctions and fusion points of the valve tissue (as pushed apart and fixed by the stent) will make sealing around the prosthetic valve difficult. In practice, this has often led to severe leakage of blood around the stent apparatus.

Other drawbacks of the Andersen '614 approach pertain to its reliance on stents as support scaffolding for the prosthetic valve. First, stents can create emboli when they expand. Second, stents are typically not effective at trapping the emboli they dislodge, either during or after deployment. Third, stents do not typically conform to the features of the native lumen in which they are placed, making a prosthetic valve housed within a stent subject to paravalvular leakage. Fourth, stents are subject to a tradeoff between strength and compressibility. Fifth, stents cannot be retrieved once deployed. Sixth, stents have an inherent strength that is not adjustable.

As to the first drawback, stents usually fall into one of two categories: self-expanding stents and balloon expandable stents. Self-expanding stents are compressed when loaded into a catheter and expand to their original, non-compressed size when released from the catheter. These are typically made of Nitinol. Balloon expandable stents are loaded into a catheter in a compressed but relaxed state. These are typically made from stainless steel or other malleable metals. A balloon is placed within the stent. Upon deployment, the catheter is retracted and the balloon inflated, thereby expanding the stent to a desired size. Both of these stent types exhibit significant force upon expansion. The force is usually strong enough to crack or deform thrombosis, thereby causing pieces of atherosclerotic plaque to dislodge and become emboli. If the stent is being implanted to treat a stenosed vessel, a certain degree of such expansion is desirable. However, if the stent is merely being implanted to displace native valves, less force may be desirable to reduce the chance of creating emboli. An additional concern related to displacing an aortic valve is the risk of conduction disturbances (i.e. left bundle branch block) due to the close proximity of the conduction pathways to the native valve structure. Excessive radial force applied at the native valve site increases the risk of irritation or damage to the conduction pathway and heart block.

As to the second drawback, if emboli are created, expanded stents usually have members that are too spaced apart to be effective to trap any dislodged material. Often, secondary precautions must be taken including the use of nets and irrigation ports.

The third drawback is due to the relative inflexibility of stents. Stents typically rely on the elastic nature of the native vessel to conform around the stent. Stents used to open a restricted vessel do not require a seal between the vessel and the stent. However, when using a stent to displace native valves and house a prosthetic valve, a seal between the stent and the vessel is necessary to prevent paravalvular leakage. Due to the non-conforming nature of stents, this seal is hard to achieve, especially when displacing stenosed valve leaflets.

The fourth drawback is the tradeoff between compressibility and strength. Stents are made stronger or larger by manufacturing them with thicker members. Stronger stents are thus not as compressible as weaker stents. Most stents suitable for use in a valve are not compressible enough to be placed in a thin catheter, such as a 18Fr catheter. Larger delivery catheters are more difficult to maneuver to a target area and also result in more trauma to the patient.

The fifth drawback of stents is that they are not easily retrievable. Once deployed, a stent may not be recompressed and drawn back into the catheter for repositioning due to the non-elastic deformation (stainless steel) or the radial force required to maintain the stent in place (Nitinol). Thus, if a physician is unsatisfied with the deployed location or orientation of a stent, there is little he or she can do to correct the problem.

The sixth drawback listed above is that stents have an inherent strength and are thus not adjustable. As previously stated, stronger stents are made with stronger members. Once a stent is selected and deployed, there is little a physician can do if the stent proves to be too strong or too weak.

Various embodiments of devices that solve these problems are introduced in U.S. Patent Publication No. 2006/0271166 to Thill et al., entitled "Stentless Support Structure," the contents of which is incorporated herein in their entirety. This publication teaches a braided mesh tube that is capable of folding back and forth into itself to build, in situ, a support structure that is strong enough to hold back the leaflets of a native valve sufficiently to successfully deploy a replacement valve, thus obviating the need for excision of the native valve. Advantageously, because of the inverting nature of these devices, the braided mesh, in an elongated delivery configuration, does not need to possess the strength to accomplish native valve displacement until the inversion process occurs. This allows the mesh tube to be constructed such that, in the elongated delivery state, the tube can be compressed into a very small catheter, such as a 18Fr or smaller catheter. Such a small catheter significantly reduces patient trauma and allows for easy percutaneous, intraluminal navigation through the blood vessels. It is to be understood that terms like transluminal and percutaneous, as used herein, are expressly defined as navigation to a target location through and axially along the lumen of a blood vessel or blood vessels as opposed to surgically cutting the target vessel or heart open and installing the device manually. It is further to be understood that the term "mesh" as used herein describes a material constructed of one or more braided or woven strands.

In order to accomplish the folding back and forth feature of this device, there are preformed, circumferential folds in the device. One embodiment has two circumferential folds that are longitudinally spaced apart in the extended configuration. One of these folds is preformed to fold inwardly, and the other is preformed to fold outwardly. These preformed folds, when released out of a catheter, tend to return to a folded configuration that has a z-like cross-section. This cross-section design results not only because the inward pre-formed fold folds inwardly and the outward pre-formed fold folds outwardly, but because these folds reverse longitudinal positions once folded. If the inward preformed fold is distal of the outward preformed fold in the extended position, in the folded position the inward preformed fold will be proximal of the outward preformed fold. This design allows a valve on a distal end of the device to be drawn into the device when folded, without requiring the valve itself to be inverted or everted. In one embodiment having two preformed folds, the inversion process thus results in a three-layered configuration that could be significantly shorter than the extended length, depending on the spacing of the folds.

In the development of the devices described in the aforementioned publication, U.S. Pat. Pub. 2006/0271166, it was found that, occasionally, it was advantageous to use an additional device to hold the outermost layer of the implant axially in place while inversion of a layer was being effected. This gave rise to the delivery tool shown and described in U.S. Patent Publication 2008/0082165 to Wilson et al., entitled "Delivery Tool For Percutaneous Delivery Of A Prosthesis." This delivery tool includes an expandable mesh region that, when axially compressed, flares outwardly to form a bulbous or rounded structure of increased radius. Further axial compression creates a flat, disc-like surface. In use, the device is extended through an implant prior to releasing the implant from the delivery catheter. The device is then expanded to the disc-like configuration and pulled proximally to act as a backstop at a desired target location, against which the implant is delivered. Thus, the disc-like device prevents axial migration of the implant in a distal direction if and when distal force is placed on the implant during inversion of the second or subsequent layers into the first layer.

It has been found, however, that in some cases, depending on target location and patient anatomy, there is insufficient space in a distal axial direction beyond the target location to efficiently use this delivery device. For example, some patients may have limited left ventricular space, which may prohibit the use of the backstop device.

There is thus a need for a device that is able to prevent axial migration of the aforementioned braided implant devices during inversion, but does not require significant space distally beyond the target location.

BRIEF SUMMARY OF THE INVENTION

The present invention meets the identified need by providing a delivery device that holds a braided implant in a desired location during inversion of a subsequent layer into a first layer. More specifically, the present invention provides a delivery device that releasably attaches at or near a first fold location, hereinafter referred to as the "aortic flare," which is a hinge point around which the inversion of the implant used with the present invention occurs.

Through attachment to the aortic flare, the delivery device of the present invention enables precise positioning and inversion by limiting advancement of a portion of the implant while continuing to advance the remainder of the device. Hence, inversion is effected at a location selected by the user, independent of patient anatomy or geometric interference. One embodiment of the invention achieves this precise positioning through attachment to a distal end of the device.

Two aspects of the present invention provide reliable performance of the delivery device of the present invention. A first aspect is an attachment mechanism that can be mounted to a braided device without requiring significant modification to the function of the braided device. This attachment mechanism provides device stabilization during the support structure inversion process. This attachment mechanism provides both attachment to the device and a release capability in some embodiments. A second aspect of the present invention includes positioning mechanisms that prevent movement of the device in the target location during the inversion process.

Another aspect of the present invention provides freedom of motion to the support structure anchors as the device is being deployed, but automatically actuates anchor locking mechanisms when the device has been advanced to the appropriate position for the inversion process. This automatic actuation reduces the need for physician involvement or judgment in the tensioning and setting of the anchor mechanisms. The nature of the mechanism also accounts for manufacturing and use tolerances, precisely tuning the anchor locking mechanism to the selected valve and delivery system.

Yet another aspect of the invention provides a deployment device that allows the positioning, implantation and deployment of a prosthetic valve such that the valve achieves complete function prior to releasing the valve. The valve may be observed and verified that it is functioning normally prior to release. If the valve is not functioning as intended, the entire device may be quickly pulled back into the delivery device. In some circumstances, the valve is able to be relocated and redeployed.

Still another aspect of the invention provides a delivery device that includes a limiter that may be set prior to or during the procedure. The limiter ensures that the braided implant does not exit the delivery device more than a desired amount, prior to inverting.

DETAILED DESCRIPTION OF THE INVENTION

Figure 1:
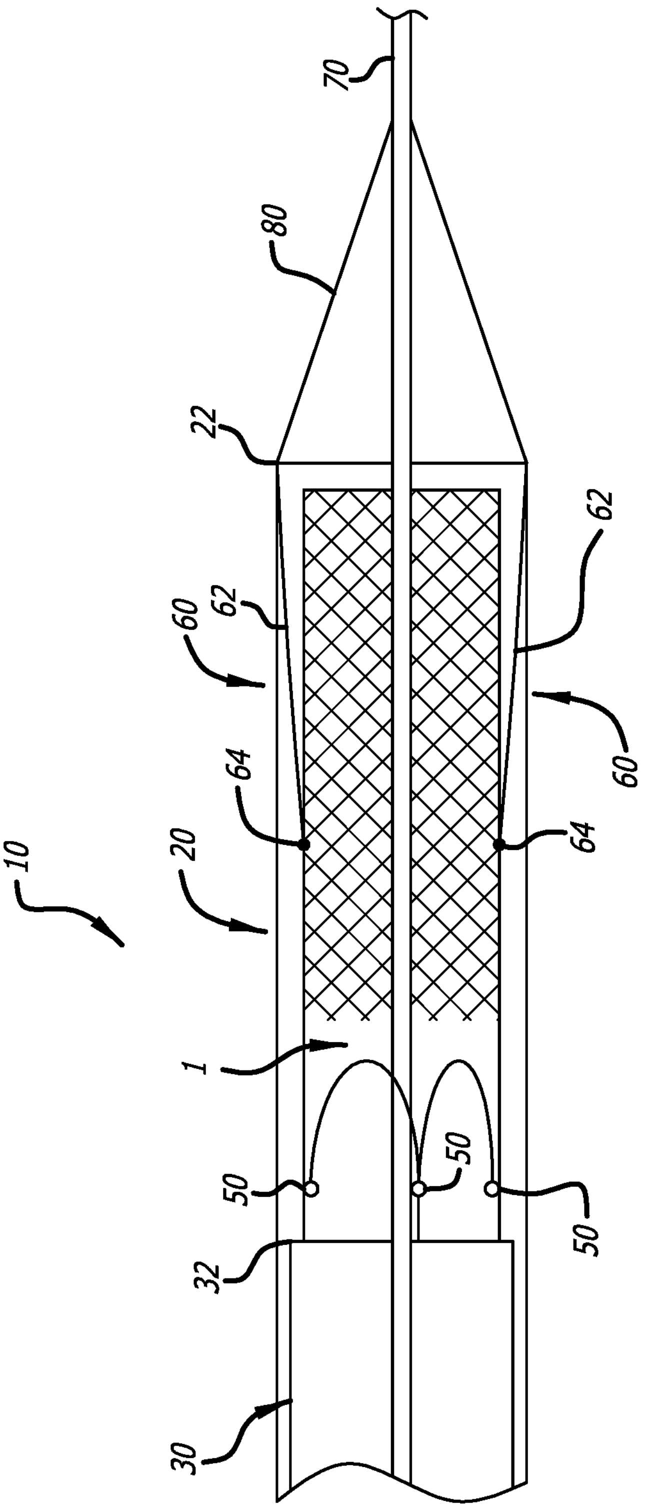
FIG. 1 is a partial cross-sectional view of an embodiment of a delivery device of the present invention with an implant loaded in a distal end thereof.

Referring now to the Figures and first to FIG. 1, there is shown a distal end of a delivery device 10 of the present invention. The delivery device generally includes a delivery catheter 20, and a pusher catheter 30 slidably contained within the delivery catheter 20. The pusher catheter 30 is preferably a multi-lumen catheter containing lumens for slidably containing and maintaining alignment of three attachment cables 40 (hereinafter "valve retention cables") (see FIG. 3), each of which has a releasable grasping mechanism 50 at a distal end thereof. The delivery device 10 also includes at least one positioning mechanism 60 used to aid the tool or implant 1 in achieving a folded, deployed configuration from an extended, unfolded, navigation configuration. In one embodiment, the at least one positioning mechanism 60 is attached to a distal end of the delivery catheter 20. In another embodiment, the at least one positioning mechanism 60 is slidably contained within the delivery catheter 20, similar to the valve retention cables 40.

The delivery catheter 20 is an external sheath defining a single lumen for housing the pusher catheter 30, the tool or implant 1, the valve retention cables 40, and the positioning mechanisms 60. The delivery catheter 20, when loaded, houses a tool or implant 1 near its distal end 22. The implant 1 is preferably an implant similar to those taught and described in U.S. Patent Publication No. 2006/0271166. The delivery catheter 20 may be formed with a preset curve at its distal end. Positive results have been achieved with a 180 degree preset curve.

The pusher catheter 30 may include up to seven lumens. Three lumens slidably house the three valve retention cables 40. In an embodiment used over-the-wire, a fourth lumen accommodates a guidewire. In yet another embodiment, three additional lumens slidably house three positioning mechanisms, described below.

Figure 2A:
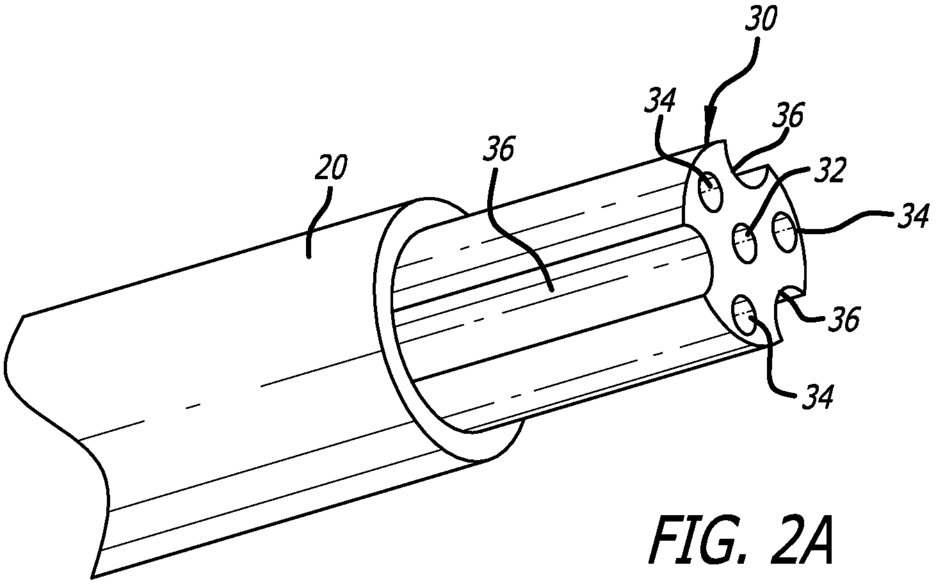
FIG. 2*a* is a perspective view of a distal end of an embodiment of a pusher catheter of the present invention.
Figure 2B:
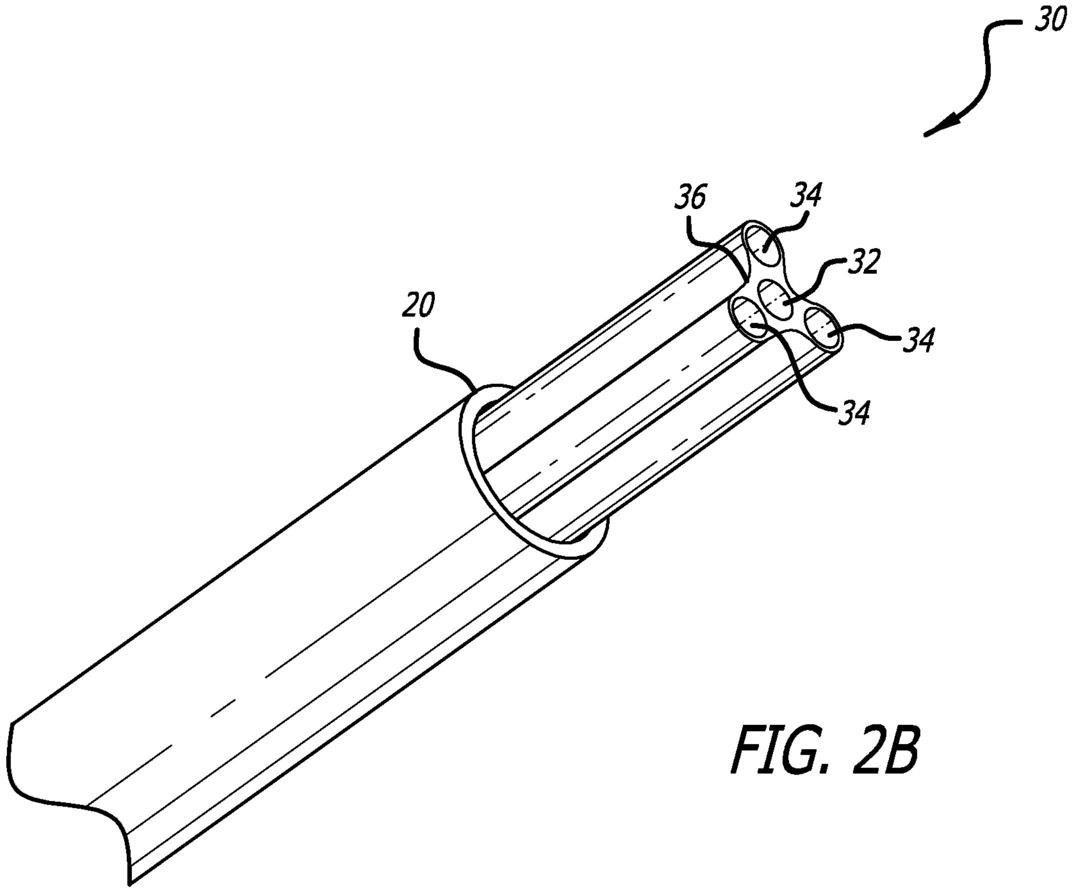
FIG. 2*b* is a perspective view of a distal end of an alternative embodiment to that of FIG. 2*a;*

FIGS. 2*a* and 2*b* show two similar embodiments of the pusher catheter 30 of the present invention defining seven lumens. The pusher catheter 30 includes a central guidewire lumen 32, and three lumens 34 that contain either the valve retention cables 40 or the positioning mechanisms described below. The remaining three lumens 36 house the remaining valve retention cables or positioning mechanisms. In order to save on space, the lumens 36 may be formed as external indentations, thereby relying on the inner wall of the delivery catheter 20 to complete the lumen and contain the remaining valve retention cables or positioning mechanisms. In a preferred embodiment, the lumens 34 contain the valve retention cables 40 and the lumens 36 contain the positioning mechanisms 60. In this embodiment, the pusher catheter 30 may continue to be advanced even if the positioning mechanisms 60 can no longer be advanced.

In one embodiment, the positioning mechanisms are small enough to fit three valve retention mechanisms, and an associated containment sheath, in a single lumen 36, leaving two other lumens 36 unused or available for use as irrigation channels.

Figure 3:
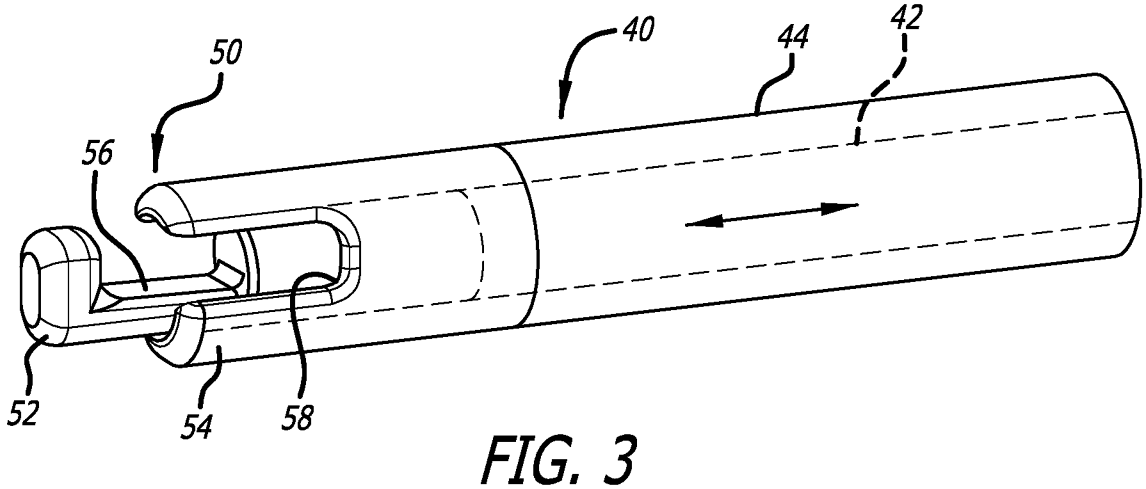
FIG. 3 is a perspective view of an embodiment of a distal end of a release mechanism of the present invention in an open configuration.
Figure 4:
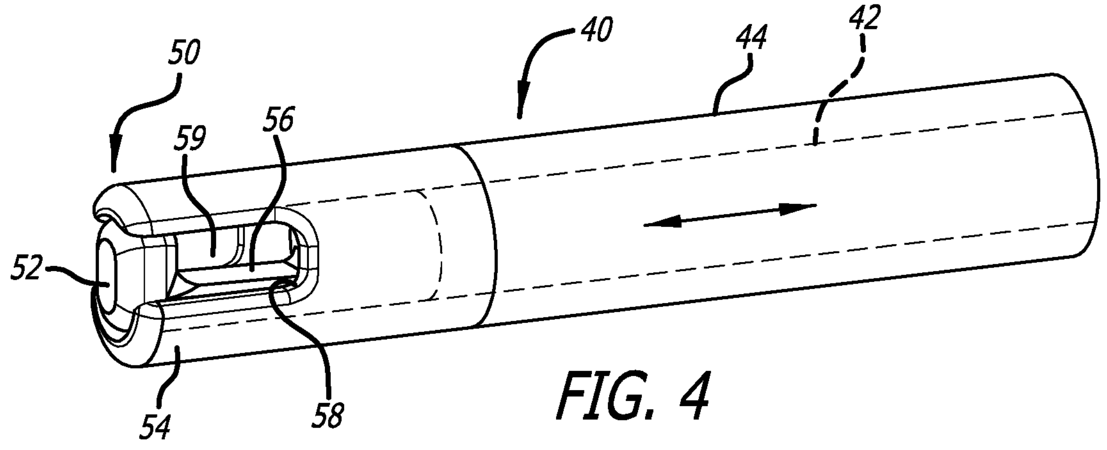
FIG. 4 is a perspective view of the mechanism of FIG. 3 in a closed configuration.

The releasable grasping mechanisms 50 may be similar to those shown and described in U.S. Pat. Pub. 2008/0082165 (at FIGS. 5-8). Another embodiment of releasable grasping mechanisms is shown in FIGS. 3 and 4. The grasping mechanisms 50 are attached to commissural points on an implant 1 when the device 10 is loaded. The grasping mechanism 50 provide the ability to retract the implant back into the device 10 in the event that the physician feels doing so is appropriate.

FIG. 3 shows a grasping mechanism 50 in an open configuration. The grasping mechanism 50 includes a hook 52 that slides within a mouth 54. The hook 52 defines a recess 56 sized to accommodate a component, such as a commissural point or a braid, of the tool or implant 1. The mouth 54 defines a slot 58 that is also sized to accommodate the component. FIG. 4 shows that when the grasping mechanism 50 is in a closed configuration, the recess 56 and the slot 58 together define a passage 59 that traps the component therein.

The grasping mechanism 50 is attached to a distal end of an valve retention cable 40. The valve retention cable 40 includes a wire 42 attached to the hook 52 and an elastomeric sheath 44 that is attached to the mouth 54. The wire 42 and the hook 52 are slidably contained within the sheath 44 and the mouth 54. The sheath 44 is elastomeric such that it is capable of being compressed longitudinally. This feature prevents accidental release of a tool or component contained within the passage 59. For example, when pulling a tool or implant back into the delivery sheath 20 during a retrieval, a load is placed on the wire 42, causing the wire to stretch. If the sheath 44 were not compressed, the wire 42 could stretch enough to cause the hook 52 to exit the mouth 54, thereby assuming the open configuration of FIG. 3. However, because the sheath 44 is compressed when the hook 52 is drawn into the mouth 54 during closing, the sheath 44 elongates when the wire 42 is stretched, thereby maintaining the closed configuration of FIG. 4.

The positioning mechanisms 60 aid in inverting the tool or component 1. In one embodiment, shown in FIGS. 1, 5 and 6, the positioning mechanisms 60 connect the delivery catheter 20 with a first inversion pre-fold point (also referred to herein as an "aortic flare") on the implant 1.

The positioning mechanisms 60 may comprise a plurality of tethers 62 and connectors 64. The tethers 62 may be any resilient strand-like material, flexible enough to invert from a navigation configuration to a deployment configuration. In the navigation configuration, as shown in FIG. 1, the tethers extend proximally from the distal end of the delivery catheter 20, to the connectors 64. In the deployment configuration, shown in FIGS. 5 and 6, the tethers 62 extend distally from the distal end of the delivery catheter 20 to the connectors 64. In one embodiment, the connectors 64 are able to grasp any individual braid or strand of an implant 1. In another embodiment, the connectors 64 are designed to grasp the intersection of two braids or strands. In yet another embodiment, the connectors 64 are able to grasp discrete attachment points (e.g. wire loops, sutures, etc.), that have been integrated into the mesh implant or tool 1. The length of the tethers 62 are at least the length of the material of the implant 1 that extends distally of the connectors 64 when the implant 1 is loaded into the delivery catheter 20. This way, the implant 1 remains completely within the delivery catheter 20 in the navigation configuration.

In another embodiment, the positioning mechanisms 60 are similar in construction to the valve retention cables 40 and releasable grasping mechanism 50. However, because the strength requirements of the positioning mechanisms 60 are less than those of the valve retention cables 40 and their releasable grasping mechanisms 50, the positioning mechanisms 60 may be smaller in diameter, thereby allowing a smaller overall delivery device 10. Rather than being attached to the distal end of the delivery catheter 20, as described above, the positioning mechanisms 60 of this embodiment are slidably contained within the lumens 36 of the pusher catheter 30 shown in FIG. 2.

Figure 5:
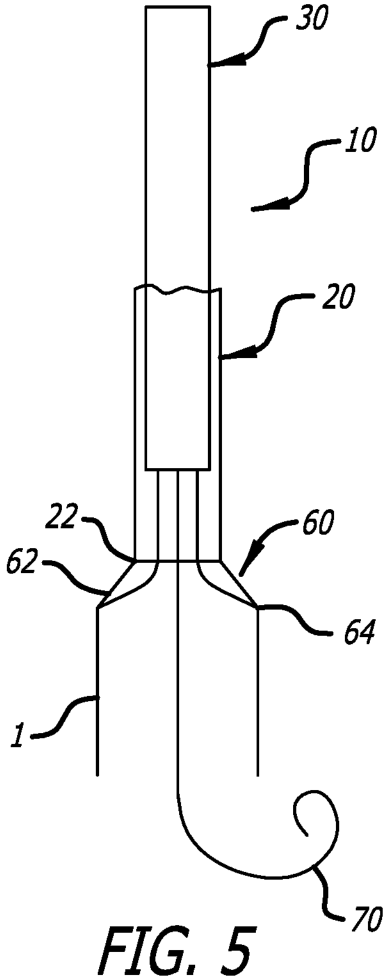
FIG. 5 is a plan cross-sectional view of an embodiment of a delivery device of the present invention, just prior to an inversion process of an implant.
Figure 6:
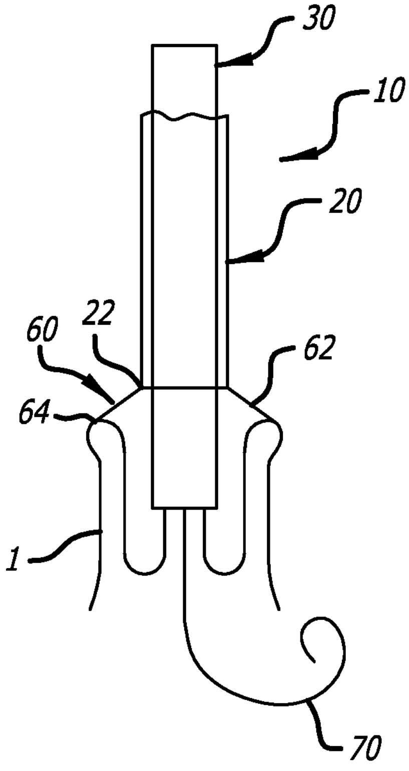
FIG. 6 is a plan cross-sectional view of an embodiment of a delivery device as shown in FIG. 1, just after the implant has been inverted.

Referring to FIGS. 5 and 6, the device 10 is designed to be able to pass over a guidewire 70 during navigation. A conical or otherwise tapered dilator tip 80 abuts against the distal end 22 of the delivery catheter 20 and is flush therewith. The dilator 80 allows the device 10 to be passed through the vasculature with minimal trauma. The dilator 80 is not physically attached to the delivery catheter 20, such that it is easily moved distally during delivery of the implant 1 to avoid interference with the deployment of the implant 1.

Having described the various components of the present invention, the various steps and configurations that occur during navigation and deployment of an implant can now be explained. FIG. 1 shows the navigation configuration of the device 10. In the navigation configuration, the implant 1 is loaded into the distal end of the delivery catheter 20 such that the implant 1 is in an elongated, non-folded state. The pusher catheter 30 is positioned within the delivery catheter 20 with its distal end 22 proximal of the implant 1. The valve retention cables 40 extend distally from the pusher catheter 30 and are connected to commissural points of the implant 1 with the releasable grasping mechanisms 50. The conical dilator 80 abuts against the distal end 22 of the delivery catheter 20. During navigation, the entire device 10 and implant 1 travel over a guidewire 70 to the target location.

FIG. 5 shows the initial stages of deployment of the implant 1. The target location has been reached and the delivery catheter 20 is retracted while the pusher catheter 30 and valve retention cables (40) remain stationary relative to the target location. Retracting the delivery catheter 20 causes the pusher catheter 30 to push the implant 1 out of the distal end 22 of the delivery catheter. As the implant 1 exits the delivery catheter 20 the implant 1 expands and the positioning mechanisms 60 are advanced through the delivery catheter 20 until the tethers 62 become taut, or in the case of the positioning mechanisms that are slidably contained within the lumens of the pusher catheter 30, the positioning mechanisms 60 can no longer be advanced.

As seen in FIG. 6, further advancement of the pusher catheter 30 causes implant material that is proximal of the connectors 64 to invert into the implant material that is distal of the connector 64. This is because the positioning mechanisms 60 are taut and do not allow further distal advancement of the implant 1. As such, the inversion of the implant 1 is urged by the preformed fold in the implant, the expansion of the memory metal making up the implant 1, and the restraint provided by the positioning mechanisms 60. Notably, the transition of the implant from initial advancement to inversion happens automatically and is dictated by the length of the tethers 64. As such, operator experience is not required to initiate inversion. Nor is there any reliance on anatomical structure to provide friction against the implant to initiate inversion.

Once the implant 1 has been fully deployed, the implant 1 is fully functional prior to release. This allows verification of proper operation of the implant 1 via one or more imaging modalities prior to full release of the implant 1. If proper operation is not achieved, the grasping mechanisms 50 can be used to pull the implant 1 back into the delivery catheter 20 such that the implant may be either removed or redeployed. If proper operation is verified, the connectors 64 are actuated to release the braids or strands of the implant 1. The pusher catheter 30 and the delivery catheter 20 are withdrawn slightly while maintaining connection with the implant 1 and the device 10 via the releasable grasping mechanism. Subsequently, the grasping mechanisms 50 are actuated to release the commissural points of the implant 1. The pusher catheter 30 is retracted into the delivery catheter 20 and the delivery catheter 20 and the guidewire 70 are withdrawn from the patient.

FIGS. 7-21 illustrate another embodiment of a delivery device 100 that is generally similar to the previously described delivery device 10, especially where noted with similar element numbers. However, the delivery device 100 includes a positioning tether assembly 110, the distal end of which is seen best in FIGS. 7-10, having a sliding release mechanism for releasing a connection to the implant 1.

More specifically, the positioning tether assembly 110 includes a plurality of tethers 104 that are each arranged in a generally closed loop. These looped tethers 104 pass through portions of the implant 1 and therefore can maintain the implant 1 in a desired position during a procedure (e.g., can prevent distal movement of the implant 1). The tethers can be disconnected from the implant 1 by releasing one end of each of the tethers 104, effectively opening the loop shape. In this respect, withdrawal of the positioning tether assembly 110 also pulls the tethers 104 out of and away from the implant 1.

Figure 7:
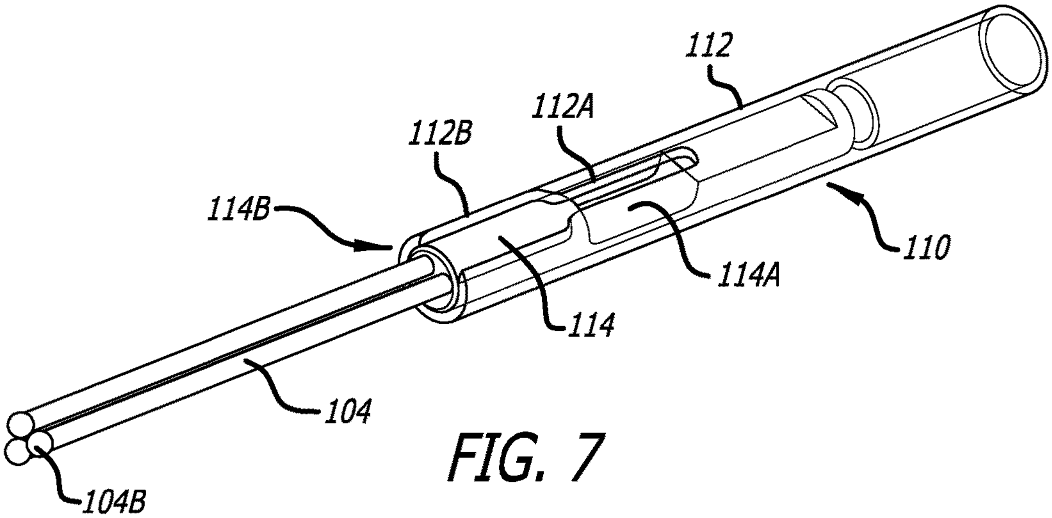
FIG. 7-10 are perspective views of a pusher catheter of an embodiment of a delivery device.
Figure 8:
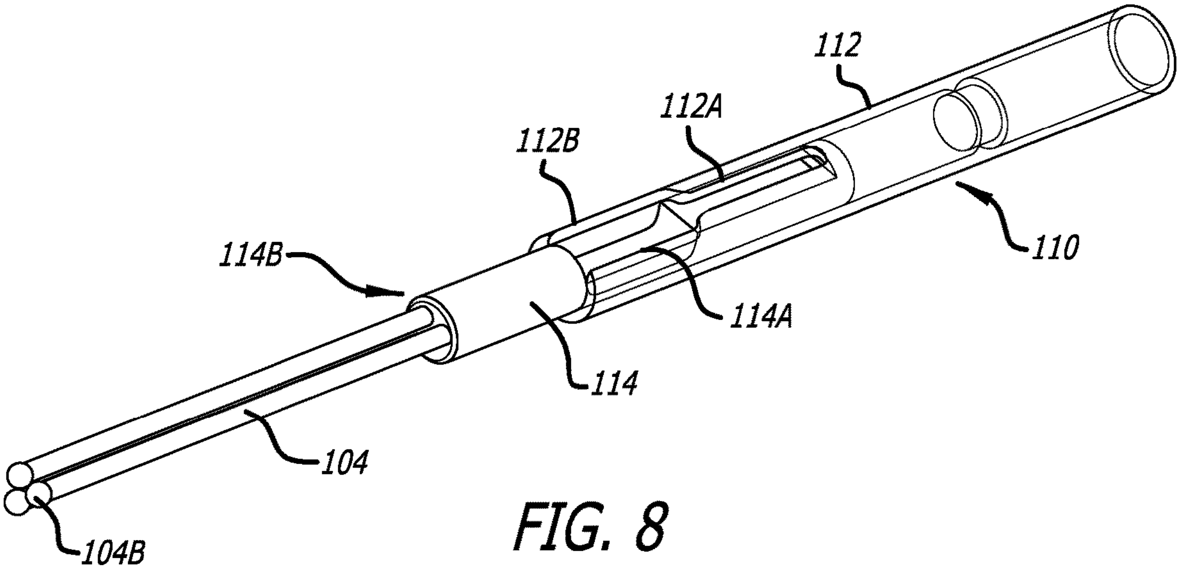
Figure 9:
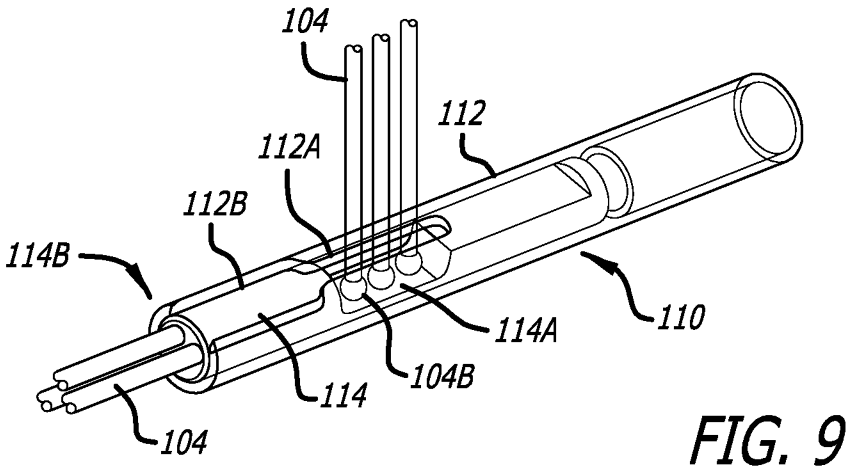
Figure 10:
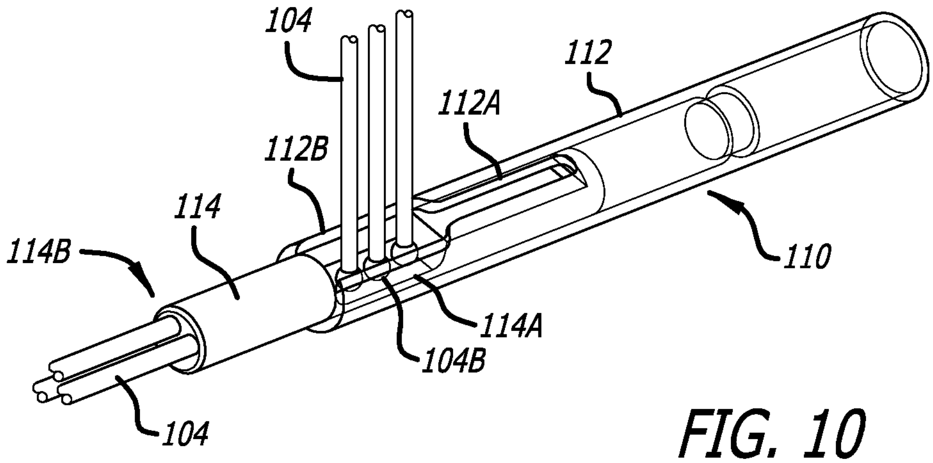
Figure 11:
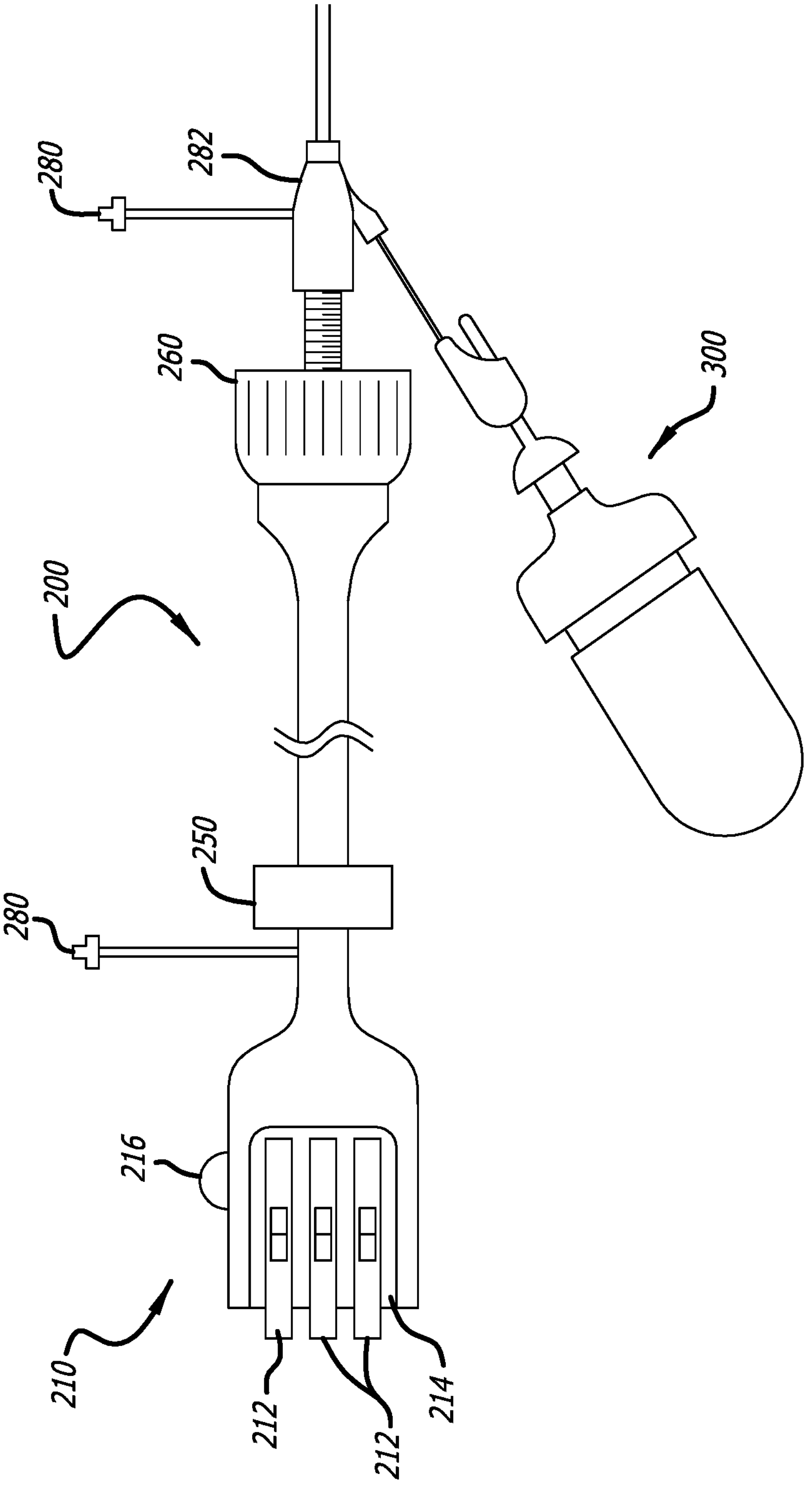
FIG. 11 is a plan view of an embodiment of a handle assembly of the invention.

The release mechanism of the positioning tether assembly 110 is triggered by advancing a sliding member 114 to the position seen in FIGS. 8 and 10 from the retracted position seen in FIGS. 7 and 9. Note that the tethers 104 are connected to a distal end 114B of the sliding member 114 (e.g., either fixed in place or pass through the member 114 back to the proximal end of the positioning tether assembly 110), but for illustrative purposes are not shown as such in FIGS. 9 and 10. Initially, the free ends 104B of the tethers 104 are located within a depression 114A of the sliding member 114 and are captured by a first slot 112A of an outer tether sheath 112. When the sliding member 114 is advanced, the depression 114A is positioned beneath a wider, second slot 1128, which allows the free ends 1048 of the tethers 104 to be released.

As best seen in FIG. 9, the free ends 104B of the tethers 104 have a generally larger size or diameter than the remaining portion of the tether 104 and can have a variety of different shapes, such as rounded, spherical or even square. The first slot 112A has a width that is large enough to accommodate the diameter of the tether 104 but is smaller than the diameter of the free ends 104B, thereby allowing the tether 104 to laterally slide within the slot 112A without the free ends 1048 from traversing through.

The second slot 112B is positioned distal to the first slot 112A and has a width that is larger than the free ends 104B. In this respect, once the depression 114A aligns under this second slot 112B, as seen in FIG. 10, the free ends 104B are released, thereby allowing the tethers 104 to assume a generally linear configuration, similar to that in FIG. 8.

While two slots are shown, a single slot may alternately be used in another embodiment. Specifically, the single slot may be similar in size to slot 112A, but extends to the distal end of the tether sheath 112. In this respect, the free ends 104B are released when the depression 114A is advanced outside of the tether sheath 112.

The positioning tether assembly 110 may be constructed with an overall outside diameter that is small enough to be slidingly contained in one of the lumens 34 or 36 of the pusher catheter 30 shown in FIG. 2*a* or 2*b*.

FIGS. 11-22 show the proximal end or handle assembly 200 of the delivery device 100. The handle assembly generally includes valve retention cable control group 210, a pusher catheter control 250, a drive mechanism 260, irrigation ports 280, and a tether control assembly 300.

The valve retention cable control group 210 includes a plurality of valve retention cable controls 212, housed in a recess 214 of the handle 200, and a locking pin 216. The individual valve retention cable controls 212 are best seen in FIGS. 12-14.

Figure 12:
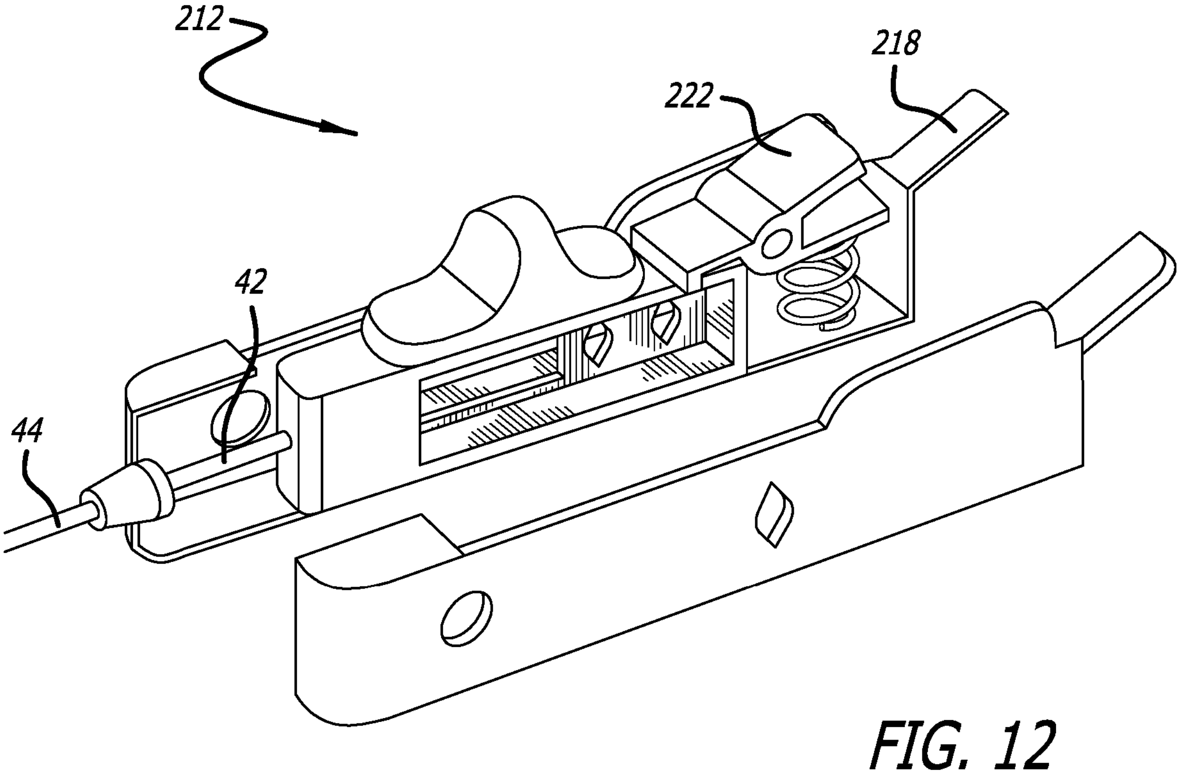
FIG. 12 is an exploded view of an embodiment of a valve retention cable control of the invention.
Figure 13:
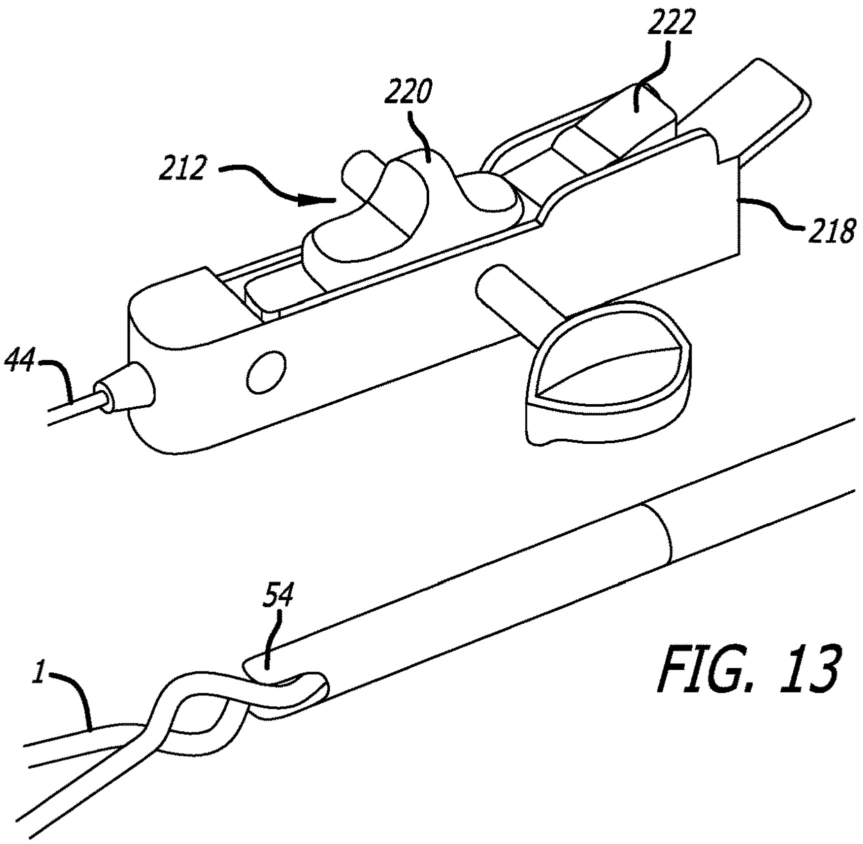
FIG. 13 is a perspective view of an embodiment of a valve retention cable control of the invention in a closed position.

FIG. 12 shows an exploded view of an individual valve retention cable control 212. The control 212 includes a housing 218, to which is attached a proximal end of the elastomeric sheath 44 of the retention cable 40 (see FIG. 3). Slidingly contained within the housing 218 is a thumb slide 220, which is connected to the wire 42 of the retention cable 40. Behind the thumb slide 220 is a spring-loaded catch 222. In operation, pulling the thumb slide rearward toward the catch 222 pulls the wire 42 relative to the sheath 44, thereby retracting the hook 52 into the mouth 54 at the distal end of the cable 40. The catch 222 maintains the retention cable 40 in a closed position. The hook 52 can be quickly released from the mouth 54 by depressing the catch 222.

Figure 14:
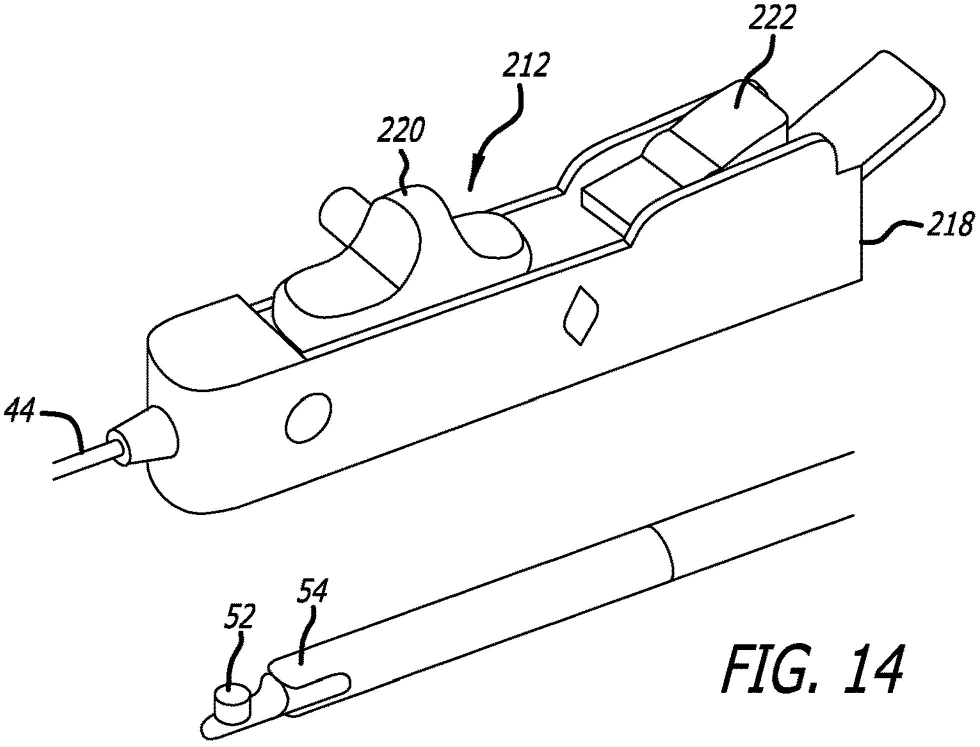
FIG. 14 is a perspective view of an embodiment of a valve retention cable control of the invention in an open position.
Figure 15:
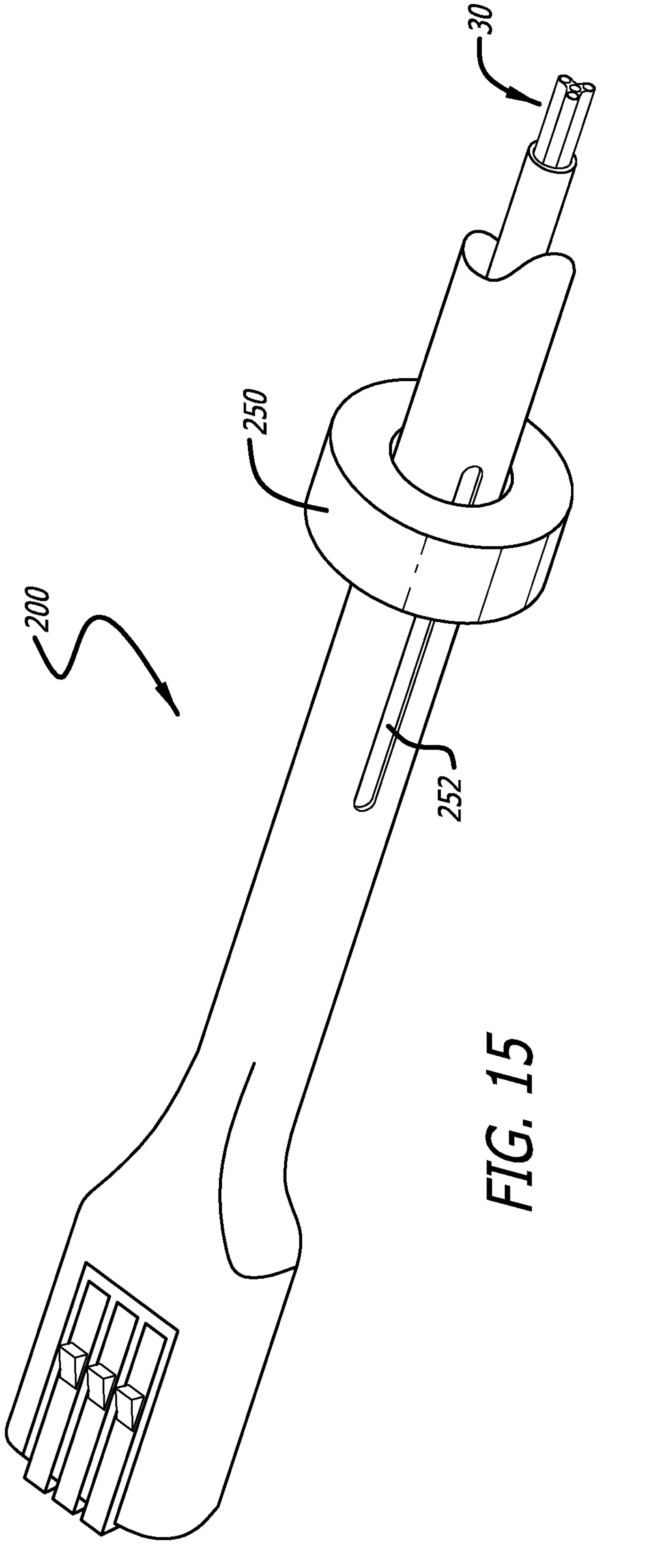
FIG. 15 is a partial perspective view of an embodiment of a handle assembly of the invention showing an embodiment of a pusher catheter control.

FIG. 14 shows the thumb slide 220 in the forward, open position. The corresponding open position of the distal end of the cable 40 is also shown. FIG. 15 shows the thumb slide 220 in the rearward, closed position. The corresponding closed position of the distal end of the cable 40 is also shown. Furthermore, a locking pin 216 has been inserted through the housing 218 and the thumb slide 220 to prevent accidental release of the implant 1 held in the mouth 54 of the retention cable 40.

Referring back to FIG. 11, it is shown that there are three controls 212 arranged in the handle 200. It can also be seen that a single locking pin 216 passes through the handle 200 and all three controls 212. This locking pin 216 is a precautionary feature that ensures none of the controls 212 are inadvertently opened. Once the valve position and operation have been verified, the physician is then able to unlock all three controls 212 by removing the single pin 216.

FIG. 15 is a partial view of the handle 200 of the device 100. FIG. 15 shows the pusher catheter control 250, which is shown as a sliding ring 250 that slides over the handle 200. The ring 250 is connected through a slot 252 in the side of the handle 200 to the pusher catheter 30. When the ring 250 is advanced to its most distal position, it may be rotated to lock the pusher catheter relative to the valve retention cables 40.

Figure 16:
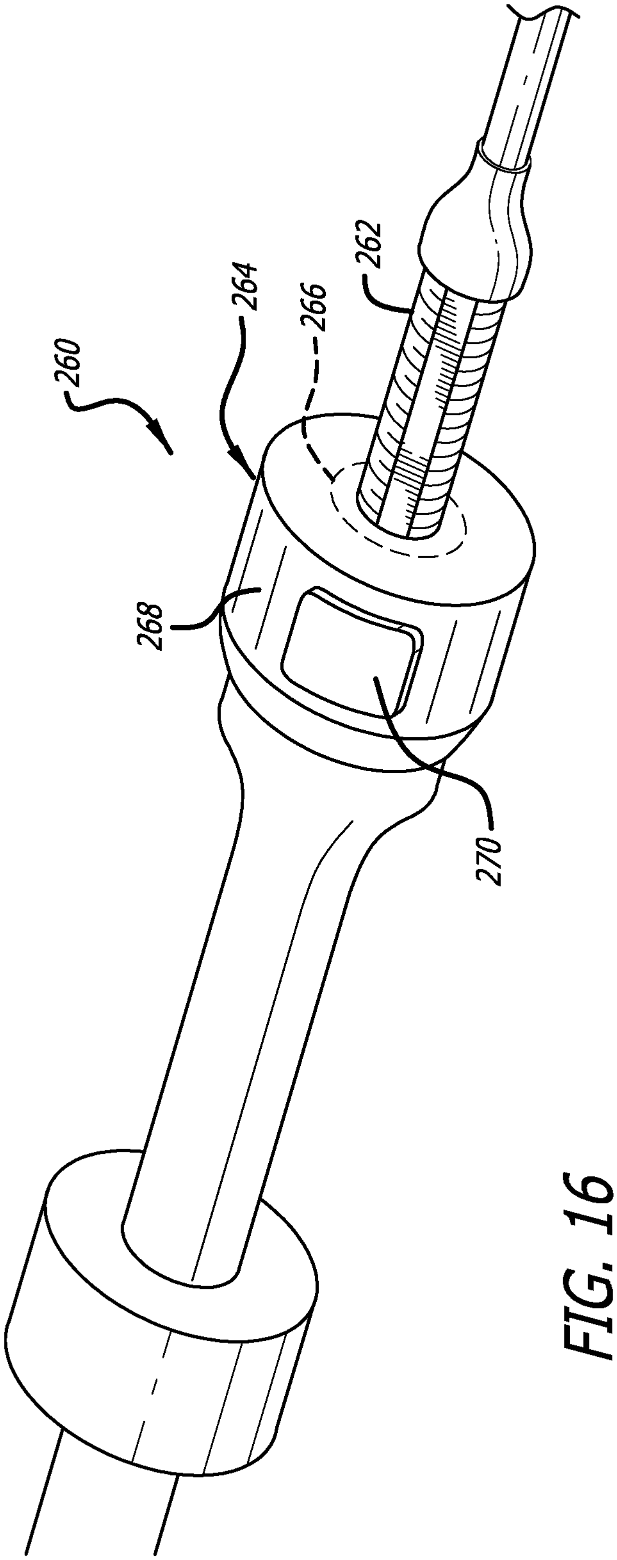
FIG. 16 is a partial perspective view of an embodiment of a handle assembly of the invention showing an embodiment of a drive mechanism.

The drive mechanism 260 is shown in FIG. 16. The drive mechanism 260 includes a lead-screw 262 and a threaded nut combination 264. The threaded nut combination 264 includes a nut 266 contained within a knob 268 and a quick release 270. Rotation of the knob 268 causes the nut 266 to act against the lead-screw 262. The knob 268 is axially fixed relative to the handle 200. The lead-screw 262 is slidingly contained within the handle 200. As such, when the nut 266 acts against the lead-screw 262, the lead-screw 262 advances or retracts in the handle 200. The lead-screw 262 is connected at its distal end to the delivery catheter 20. The rotatable threaded nut combination 264 thus allows precise control over the relative motion between the pusher catheter 30 and the delivery catheter 20. The quick release 270 may be in the form of a button or lever that disengages the nut 266 from the threads of the lead-screw 262 to allow the pusher catheter 30 and valve retention cables 40 to be quickly retracted into the delivery catheter 20.

It has been found that retracting an implant back into the delivery catheter 20 is more successful when done quickly. A slow retraction increases the risk that the catheter may buckle. As such, the handle 200 has been designed to effect a quick retraction of an implant back into the device 100 when necessary. This is accomplished by ensuring the ring 250 is rotated into the locked position so that when the handle is retracted relative to the delivery catheter, the pusher catheter 30 and the valve retention cables 40 are fixed relative to each other and thus retracted simultaneously. Depressing the quick release 270 while pulling on the knob 268 while holding the delivery catheter 20 stable causes the implant to be quickly drawn back into the delivery catheter 20.

The various components of the tether control assembly 300 are shown in FIGS. 17-21. The tether control assembly 300 generally includes a tether release controller 310 and a tether positioning mechanism 340.

Figure 17:
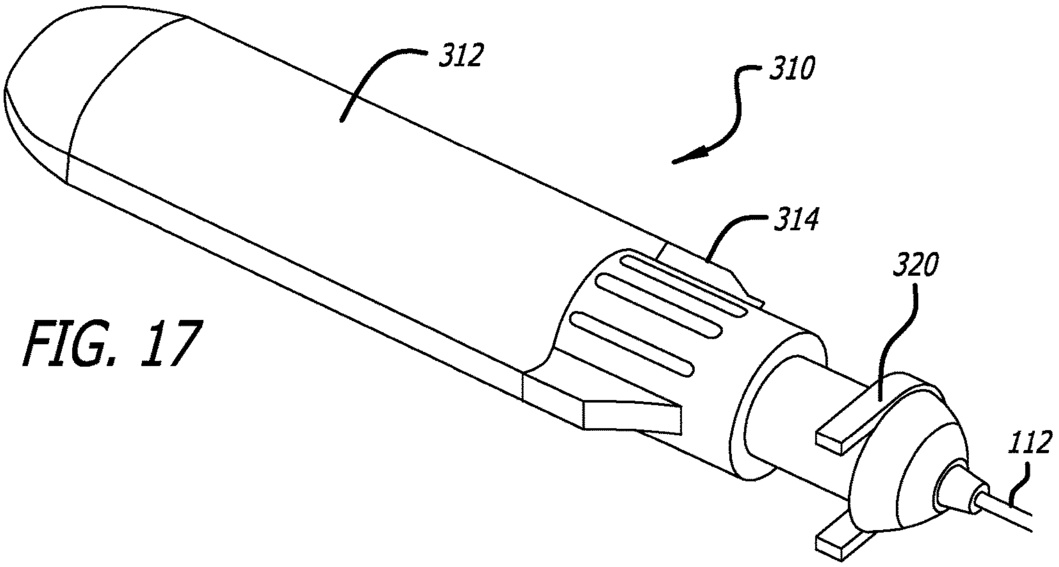
FIG. 17 is a perspective view of an embodiment of a tether release controller of the invention in a closed position.
Figure 18:
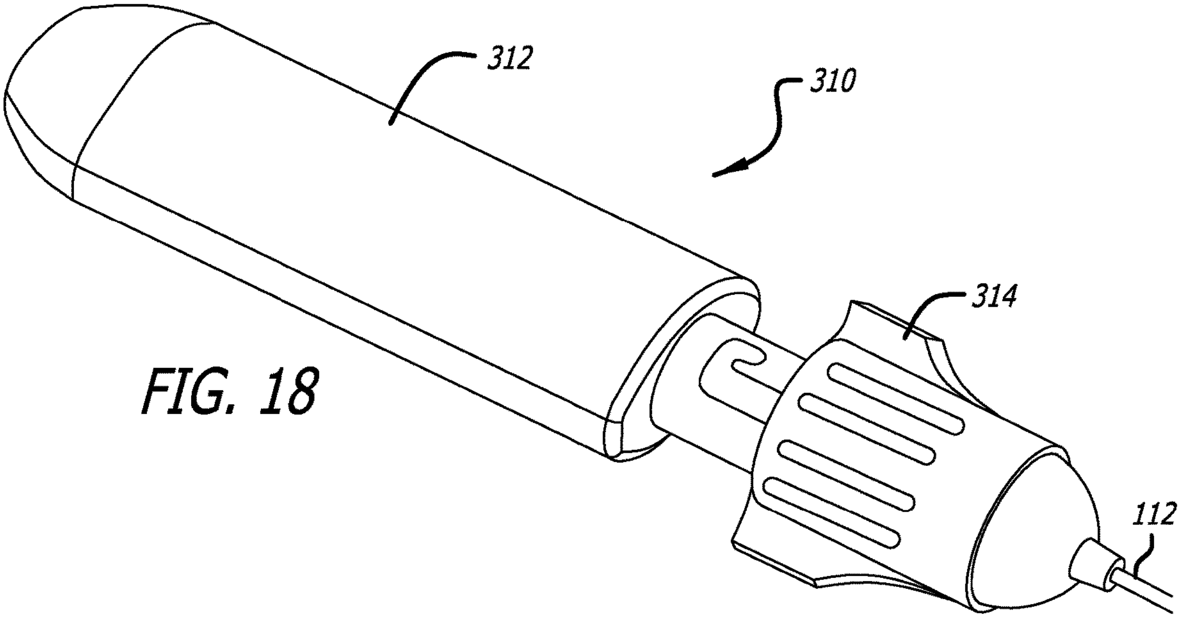
FIG. 18 is a perspective view of an embodiment of a tether release controller of the invention in an open position.

The tether release controller 310 is shown in FIGS. 17 and 18 and includes a housing 312 and a control knob 314. The housing 312 is fixed to the proximal end of the outer tether sheath 112 (See FIGS. 9 and 10) of the positioning tether assembly 110. The control knob 314 is able to slide axially, relative to the housing 312, and is attached to the proximal end of sliding member 114 (FIGS. 9 and 10). Thus, when the control knob 314 is in the forward position shown in FIG. 18, the tethers are released. When the control knob 314 is in the rearward position shown in FIG. 17, the tethers ends are trapped in the first slot 112A of the outer tether sheath 112. In the embodiment shown in the Figures, the control knob 314 can be turned in the closed position, thereby locking it closed. Also includes is a clip 320 which may be used to prevent the control knob 314 from advancing to the open position in the event it is accidentally actuated. The clip 320 is easily removed when it is desired to release the tethers.

Figure 19:
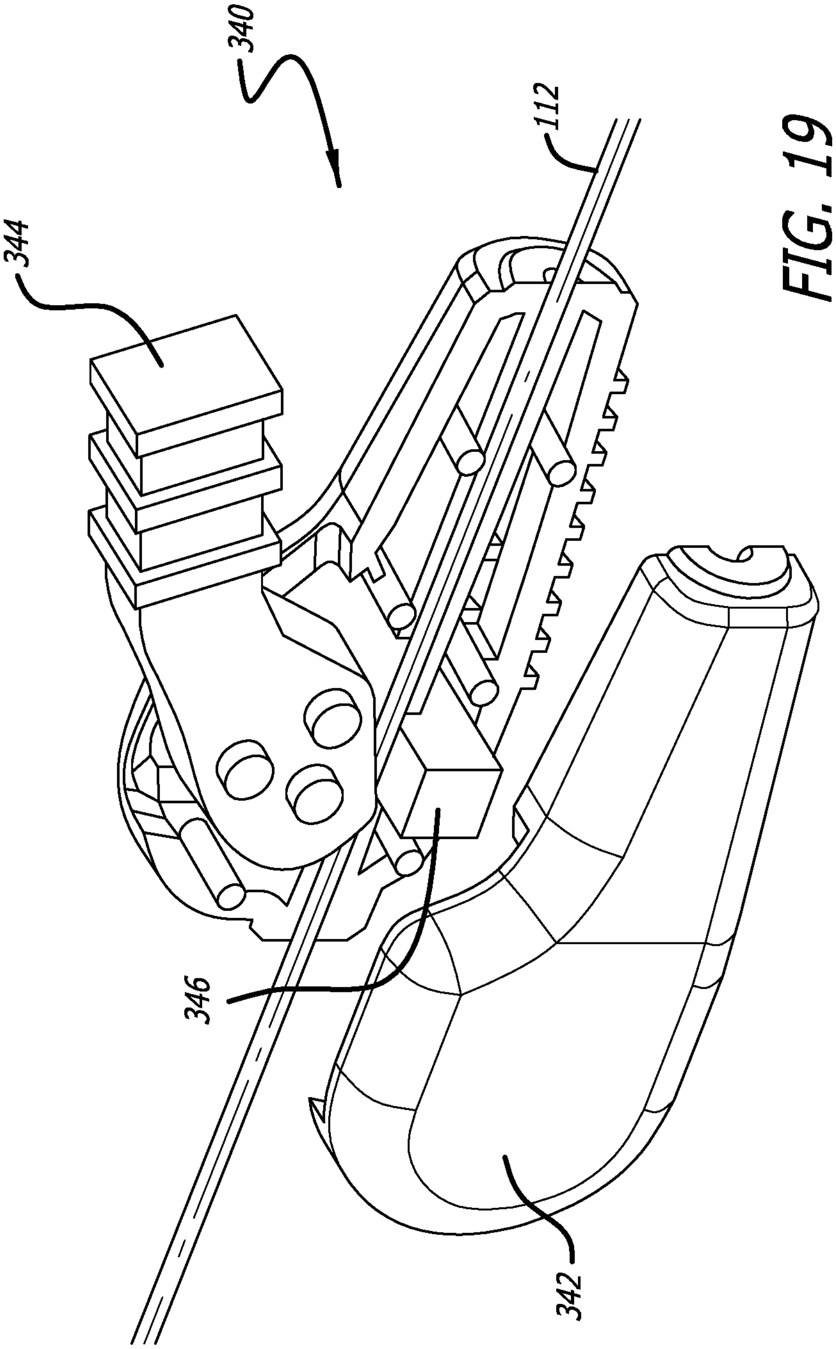
FIG. 19 is an exploded view of an embodiment of a tether positioning mechanism of the invention.
Figure 20:
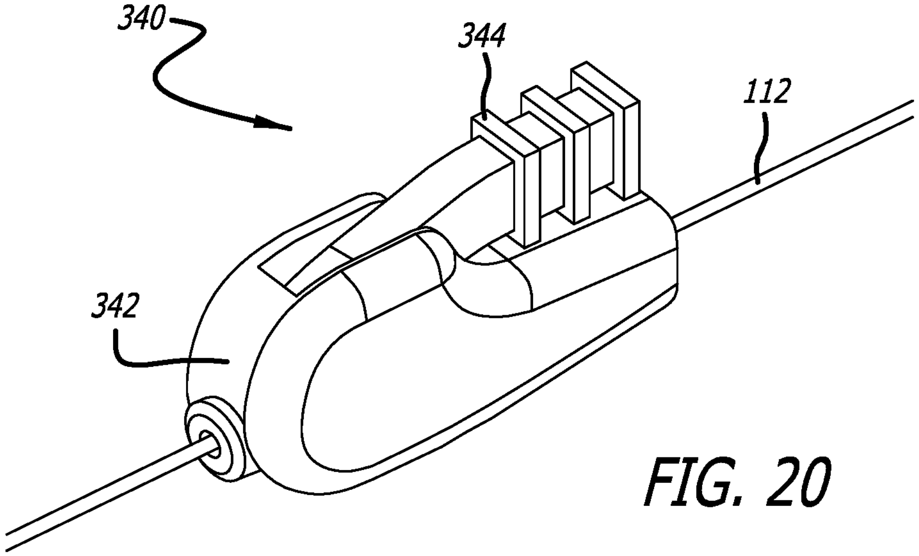
FIG. 20 is a perspective view of an embodiment of a tether positioning mechanism of the invention in a locked position.
Figure 21:
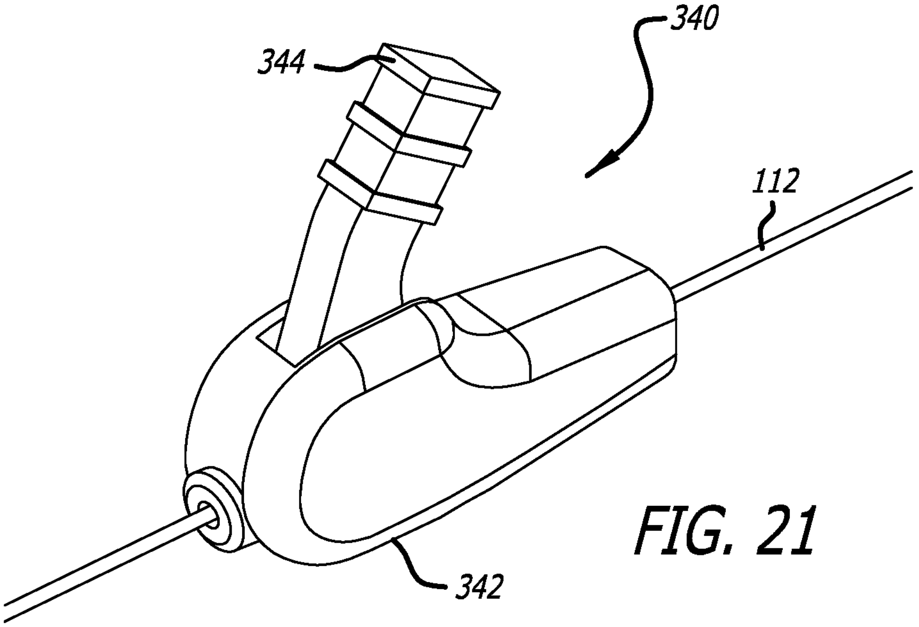
FIG. 21 is a perspective view of an embodiment of a tether positioning mechanism of the invention in an unlocked position.

FIGS. 19-21 show the tether positioning mechanism 340. The tether positioning mechanism is a slide-lock that includes a housing 342, a lever 344, and a clamp block 346. The housing 342 passes over the outer tether sheath 112 and keeps the tether sheath positioned between the lever 344 and the clamp block 346. When the lever 344 is lowered to the closed position, shown in FIG. 20, the outer tether sheath 112, and the tethers contained therein, are clamped between the lever 344 and the block 346, and cannot slide. Thus the tether positioning mechanism 340 is fixed relative to the outer tether sheath 112. When the lever 344 is in the open position, the tether positioning mechanism 340 is able to slide over the outer tether sheath 112.

FIGS. 22-29 illustrate how the delivery device 100 can be used to deliver an implant 1 according to the present invention. First, an implant 1 is loaded into the delivery device 100. After the selected valve is rinsed, each of the three valve retention cables 40 are individually attached to each of three wire form eyelets on the implant. This is accomplished by opening the valve retention cable control 212, pushing the thumb slide 220 forward to expose the hook 52 from the mouth 54. The hook 52 is placed through the wire form eyelet and the thumb slide 220 is retracted rearwardly until it engaged the catch 222. Doing so locks the slide 220 and closes the hook 52 into the mouth 54. It also compresses the outer elastomeric sheath 44 of the valve retention cable 40 to maintain interference between the hook 52 and the mouth 54, even if a pulling force is placed on the cable sufficient to stretch the cable, thereby preventing accidental release during a retrieval procedure.

After all three valve retention cables 40 are attached, the position tethers 104 are attached to the implant 1. (Alternatively, the position tethers 104 may be attached prior to the valve retention cables 40). This is accomplished by threading each of the three tethers 104 through the center of the implant and through a ventricular loop of the implant's support structure at 120 degree intervals from the inside to the outside of the implant. Once all three tethers 104 have been threaded, they are passed back up through the valve and the three tethers 104 are locked within the slot 112A of the outer tether sheath 112. Locking is accomplished by pulling the control knob 314 and rotating it to the locked position shown in FIG. 17.

Next the pusher catheter 30 is pushed forward to capture the valve retention cables 40. At the distal-most position of the pusher catheter control ring 250, the ring 250 is rotated to lock the position of the pusher catheter 30 relative to the valve retention cables 40.

The implant 1 is now ready for loading into the delivery catheter 20. The delivery catheter 20 is advanced by rotating the drive knob 268 toward the user, and the implant 1 is slowly drawn into the distal end of the delivery catheter 20. While the implant 1 is being loaded, the position of the implant is noted so an observation can be made as to when the implant has achieved the orientation in which the implant would be exposed enough from the delivery catheter 20 to be able to invert into itself. At this point the tether positioning mechanism 340, which is in the unlocked position, is slid down the sheath 112 until it contacts the delivery catheter manifold 282 (FIG. 11) and the lever 344 is moved to the locked position.

Continued loading of the implant into the delivery catheter 20 causes the tethers 104 and the tether sheath 112 to retract and the tether positioning mechanism 340 to move proximally relative to the delivery catheter manifold 282. The implant is fully loaded when the dilator tip 80 has been partially retracted into the delivery catheter 20 and there is a smooth transition between the dilator tip and the delivery catheter tip.

Figure 22:
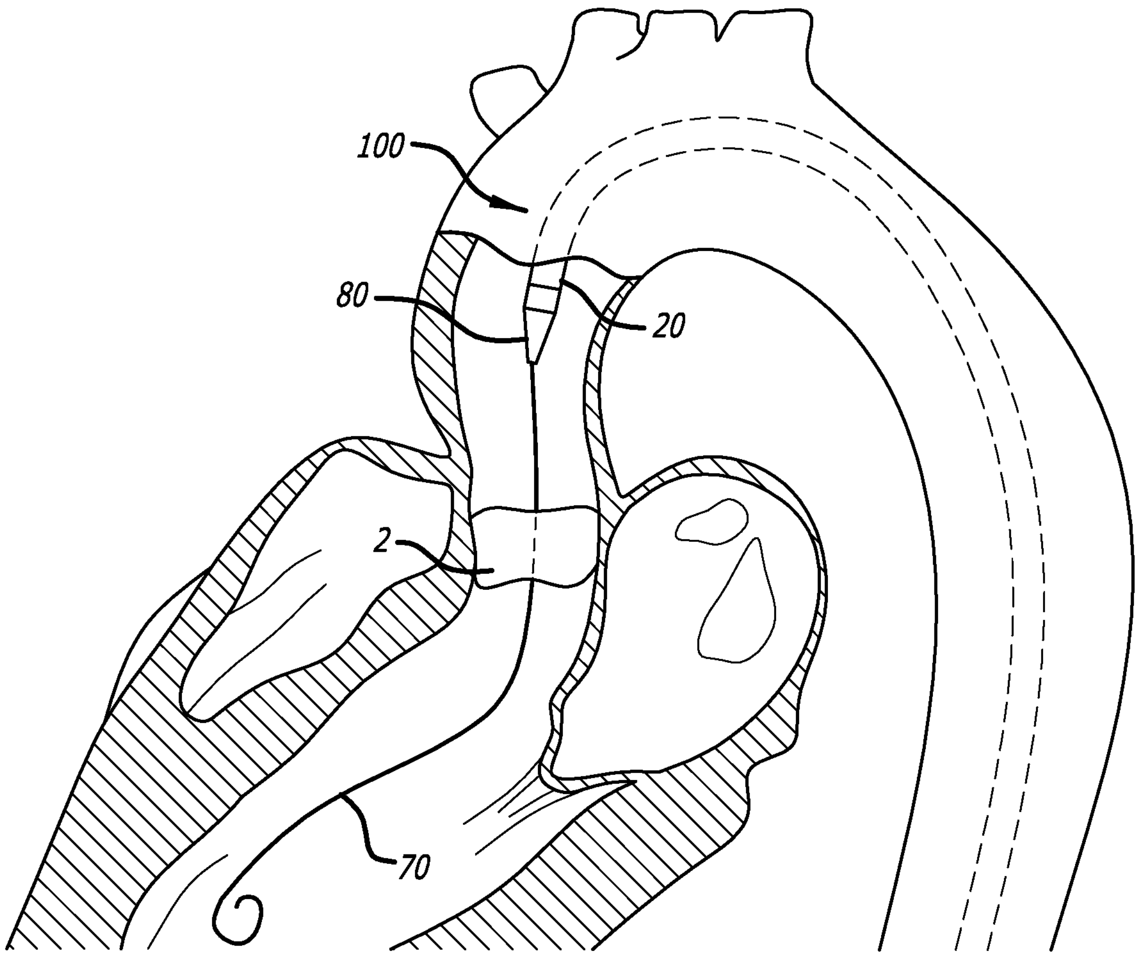
FIG. 22 is a side view of an embodiment of a delivery device of the present invention in a vessel of a patient.
Figure 23:
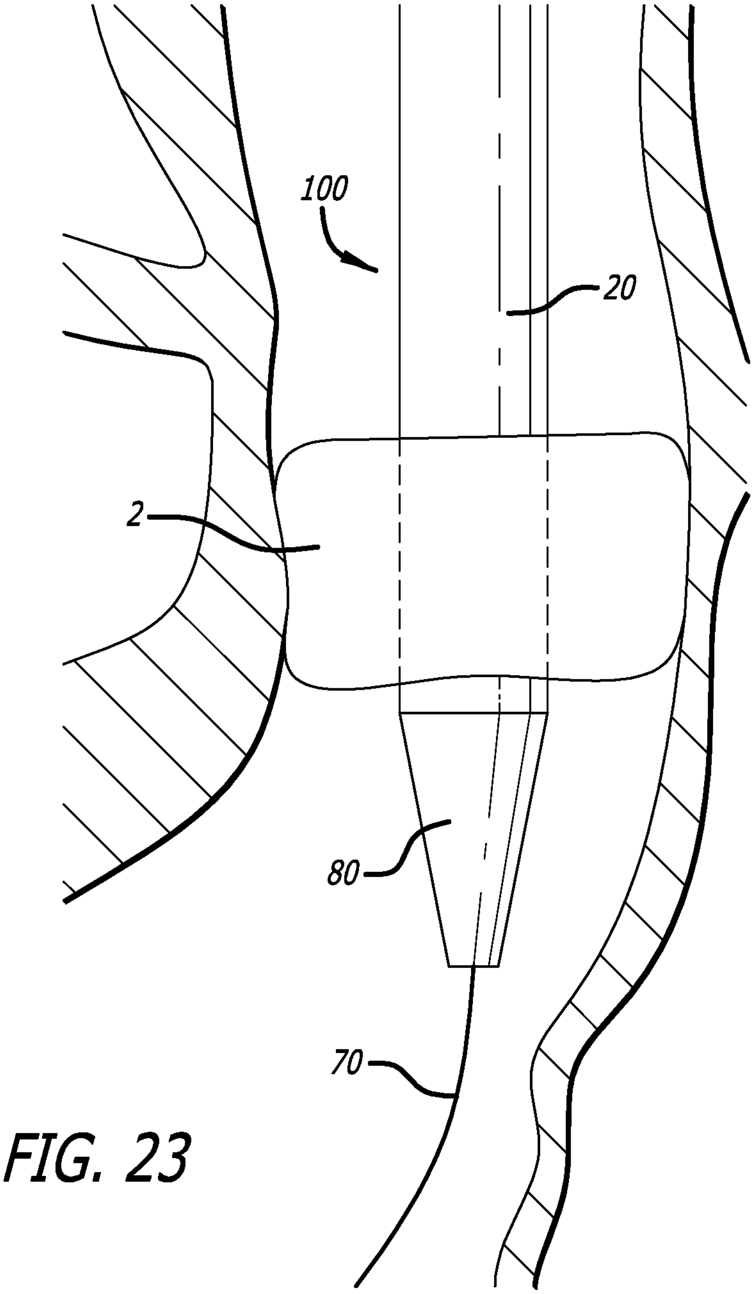
FIG. 23 is a side view of an embodiment of a delivery device as shown in FIG. 22, just after crossing a heart valve.

As seen in FIG. 22, a guidewire 70 is placed across the native aortic valve of the patient and extends out through the vascular introducer at the femoral artery access site. The proximal end of the guidewire is inserted into the dilator tip 80 of the loaded delivery system and the system is advanced over the guidewire until the guidewire is visible through the proximal end of the delivery system. The proximal end of the guidewire is then held stationary in order to maintain the position of the wire in the left ventricle of the patient and the delivery system is advanced into the vasculature through the introducer and across the native aortic valve 4 (seen best in FIG. 23). The guidewire passes through lumen 32 of the pusher catheter 30.

Figure 24:
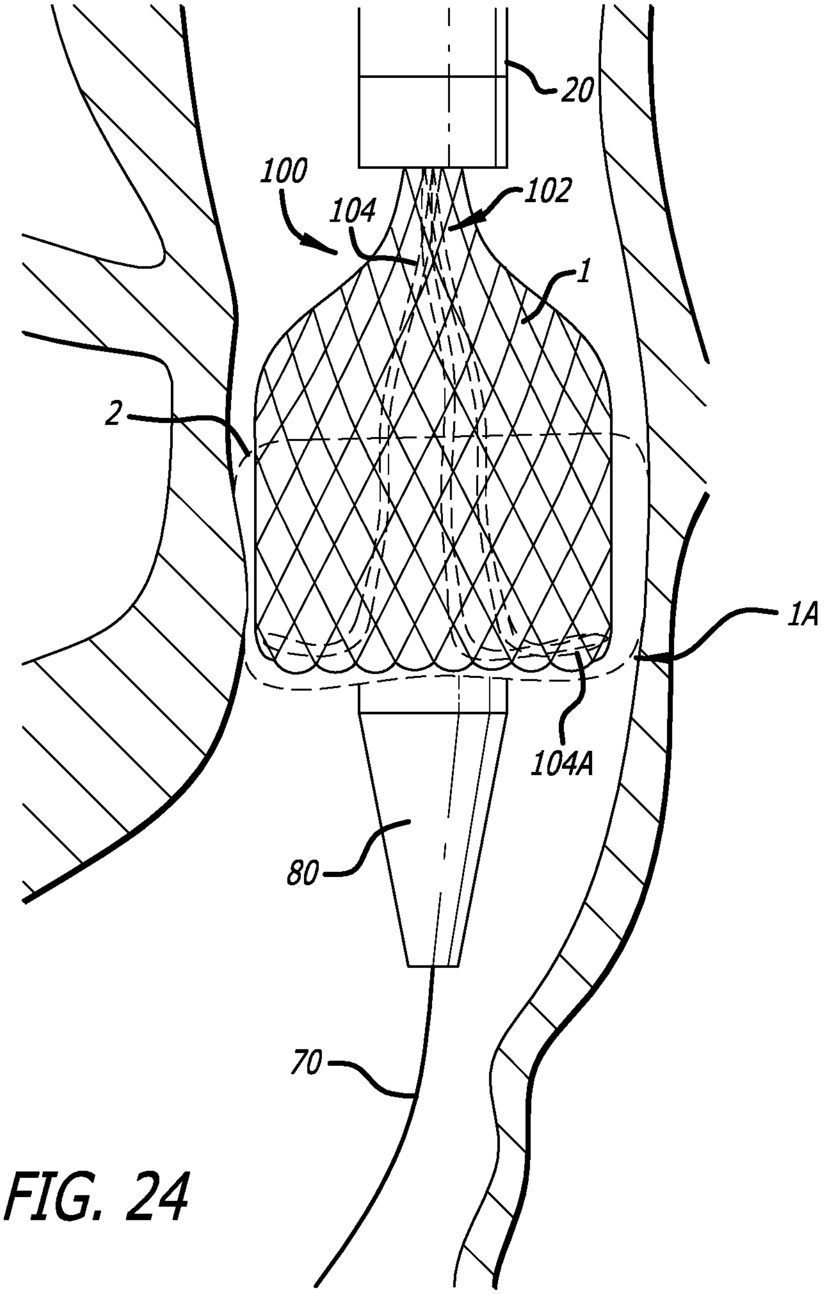
FIG. 24 is a side view of an embodiment of a delivery device as shown in FIG. 22, in which an implant is partially deployed.

Turning to FIG. 24, the delivery sheath 20 is proximally retracted to expose a portion of the implant 1 and the tethers 104. This is accomplished by rotating the drive knob 268. As the implant 1 becomes exposed, it self-expands outward against the native valve 4. During deployment, the operator maintains the implant position within the native valve of the patient. If, however, the implant is pulled too high or pushed too low relative to the native valve, the implant can be recaptured by reversing the direction of the drive knob 268 rotation, which draws the implant back into the sheath 20 for repositioning.

Figure 25:
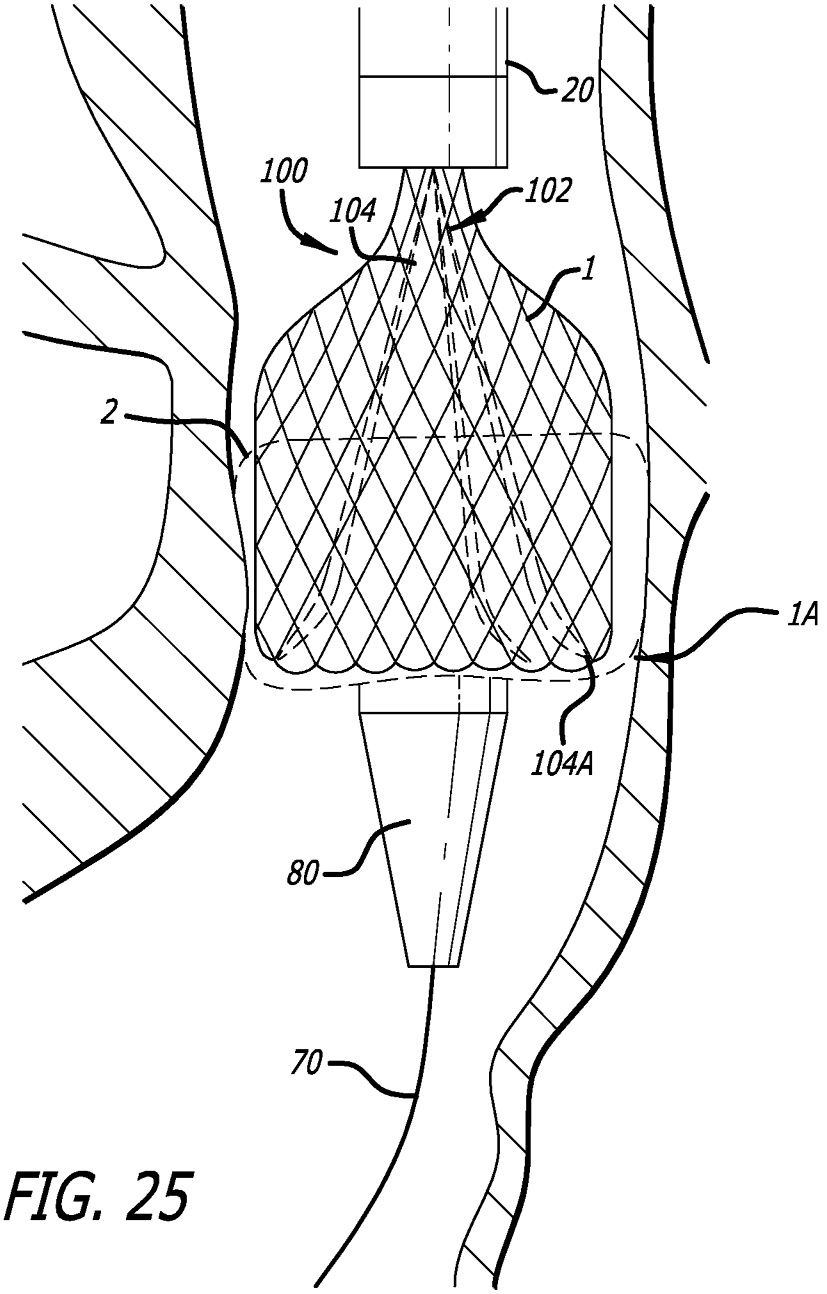
FIG. 25 is a side view of an embodiment of a delivery device as shown in FIG. 22, in which the tethers are tightened.
Figure 26:
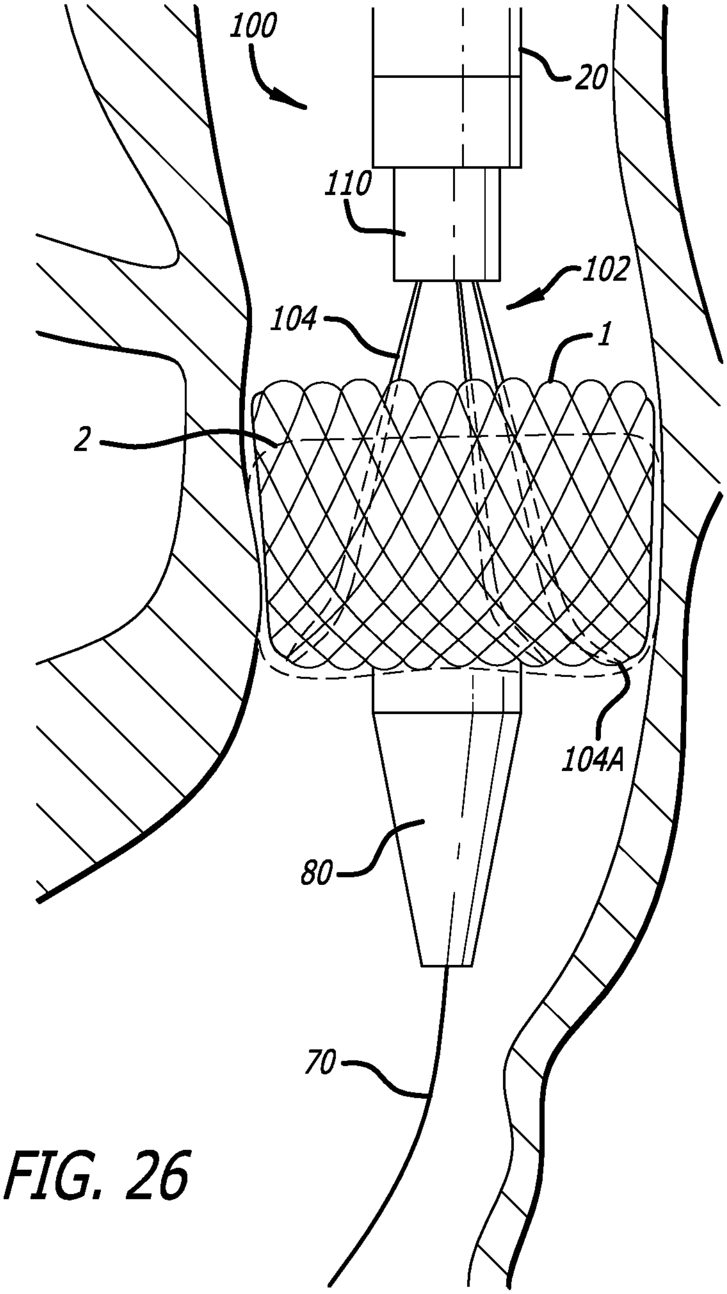
FIG. 26 is a side view of an embodiment of a delivery device as shown in FIG. 22, just after the implant has been inverted.
Figure 27:
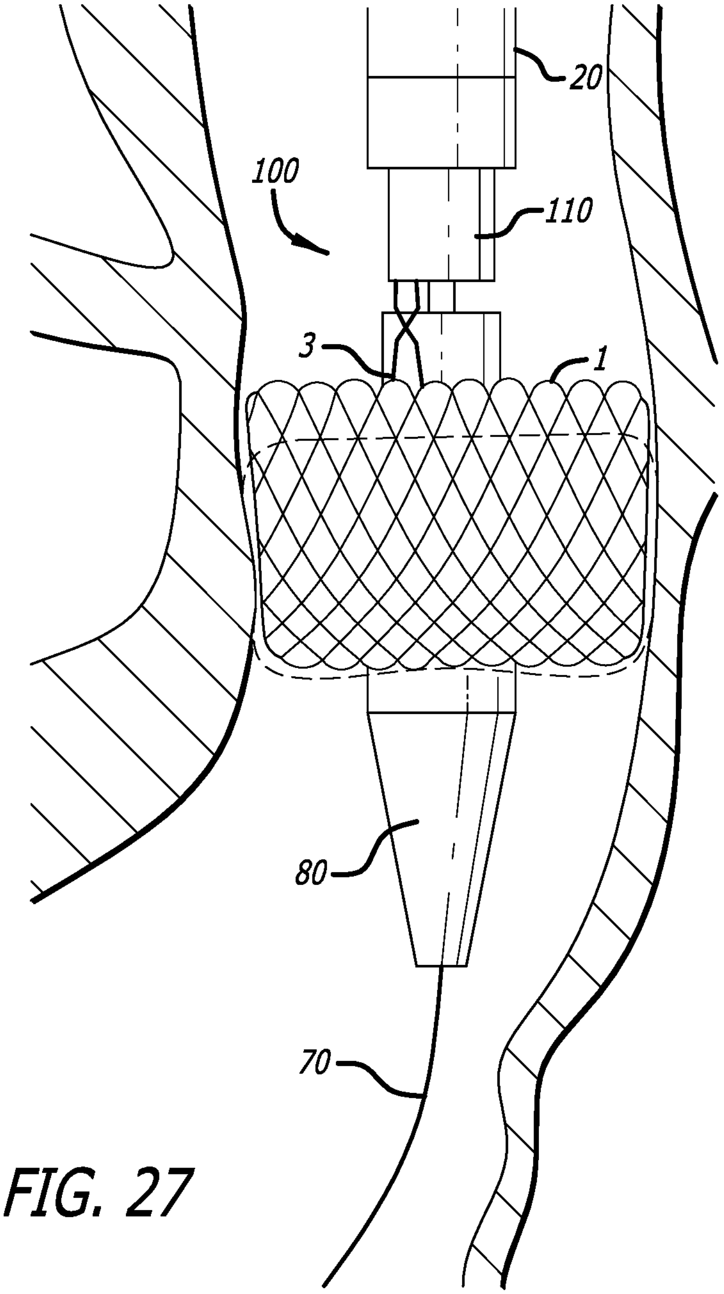
FIG. 27 is a side view of an embodiment of a delivery device as shown in FIG. 22, just after releasing and withdrawing the tethers from the implant.

As shown in FIG. 25, next, the implant 1 is folded or inverted on itself by restraining the implant with the tethers 104 and pushing a proximal portion of the implant in a distal direction with the pusher catheter 110. More specifically, when the first layer of the implant has been deployed, the tether positioning mechanism 340 will have reached the delivery catheter manifold. This freezes the position of the ventricular loops (the distal end) of the implant such that further advancement of the implant will result in a shortening and flaring of the implant in preparation for valve invention.

This flaring aspect of the valve deployment has been described as the anchoring phase, as the implant has expanded to contact the native valve tissue and the aortic flare of the device provides substantial resistance to migration. Once the anchoring phase has begun, the delivery catheter 20 is advanced through the access site and the patient vasculature. Doing so aligns the distal tip of the delivery catheter coaxial to the native valve with the curve of the delivery catheter 20 filling the outer curvature of the native aortic arch.

After the catheter 20 has been advanced, continued deployment of the valve using the drive knob is used to produce implant invention. The act of inverting the implant also deploys the tissue valve component of the implant. Once the implant has been inverted the valve begins to function, but that function is somewhat constrained due to the proximity of the tethers and the valve control cables.

After inversion has been accomplished, the user releases the tethers. First the tether positioning mechanism 340 is released by releasing the lever 344, separating it from the clamp block 346. The tether positioning mechanism 340 is free to float along the outer tether sheath 112. The drive knob 268 is rotated to further back the delivery catheter 20 away from the implant. Once the delivery catheter 20 is fully retracted, the tethers 104 can be removed by rotating and releasing the tension in the control knob 314 of the tether release controller 310. Gently pulling on the tether release controller 310 will separate the tethers 104 from the implant.

Figure 28:
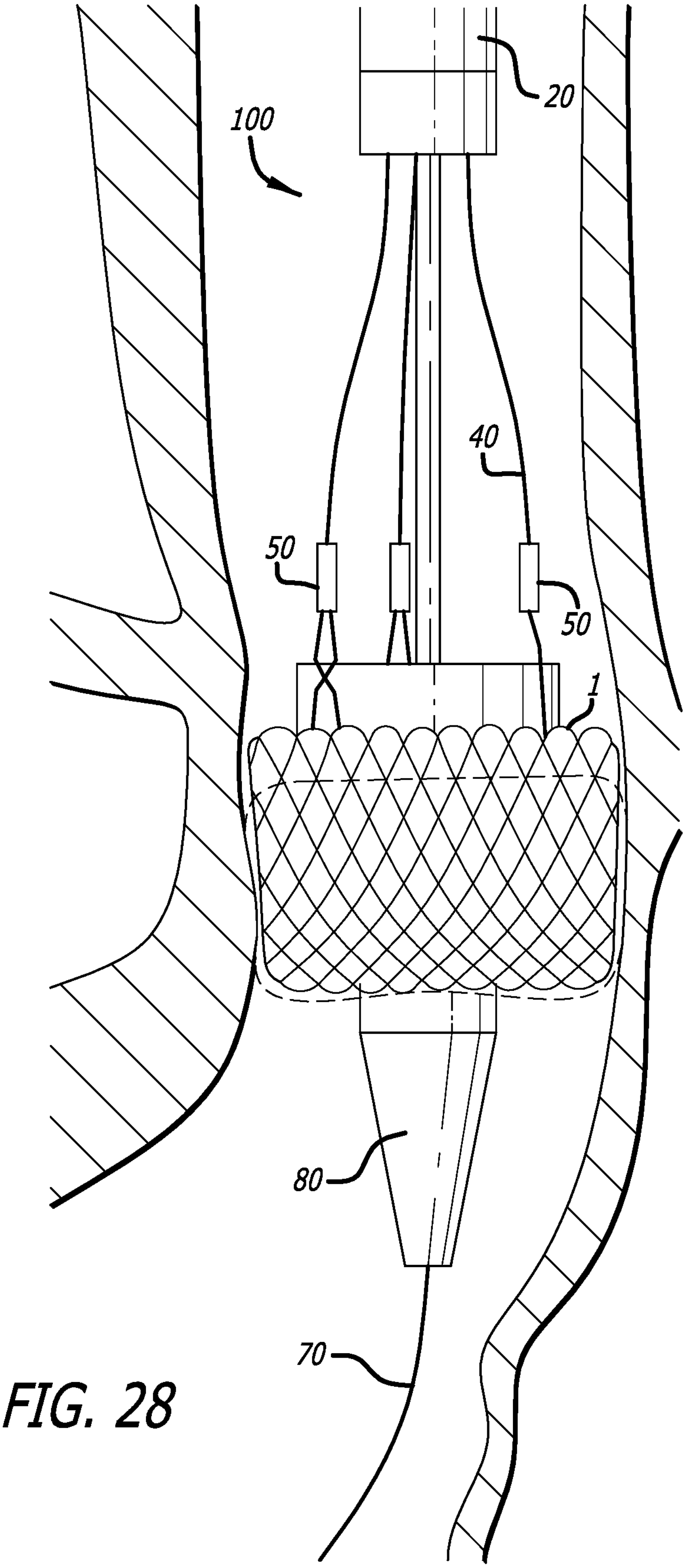
FIG. 28 is a side view of an embodiment of a delivery device as shown in FIG. 22, just prior to releasing the attachment cables; and, FIG. 29 is a side view of an embodiment of the implant, just after release of the attachment cables.

Once the tethers 104 have been removed, only the valve retention cables 40 remain connected to the implant 1, as seen in FIG. 28. As previously discussed, these cables 40 are attached to a proximal feature on the implant (e.g., the commissural points) and allow the physician to completely retract the implant 1 back into the delivery device 100 if a problem arises during the delivery procedure. Specifically, in order to observe full valve function without releasing the implant, the physician beings by rotating the ring 250 away from the operator and sliding the ring 250 in a proximal direction, retracting the pusher catheter 30. With the pusher catheter 30 retracted, the prosthetic valve now begins to function fully. The remaining attachment of the delivery system to the implant via the valve retention cables 40 has little effect on the functionality of the implant.

Once satisfied, the physician next releases the implant by pulling the locking pin 216 at the proximal end of the handle assembly 200. With the locking pin 216 removed, each of the three valve retention cable controllers 212 can be sequentially released. This is accomplished by depressing the catch 222 and sliding the thumb slide 220 forward, releasing the implant 1. Each cable can be individually retracted into the delivery catheter after it has been disengaged. When all three cables are released, the valve is fully implanted and the delivery system may be removed from the vascular introducer of the patient.

Figure 29:
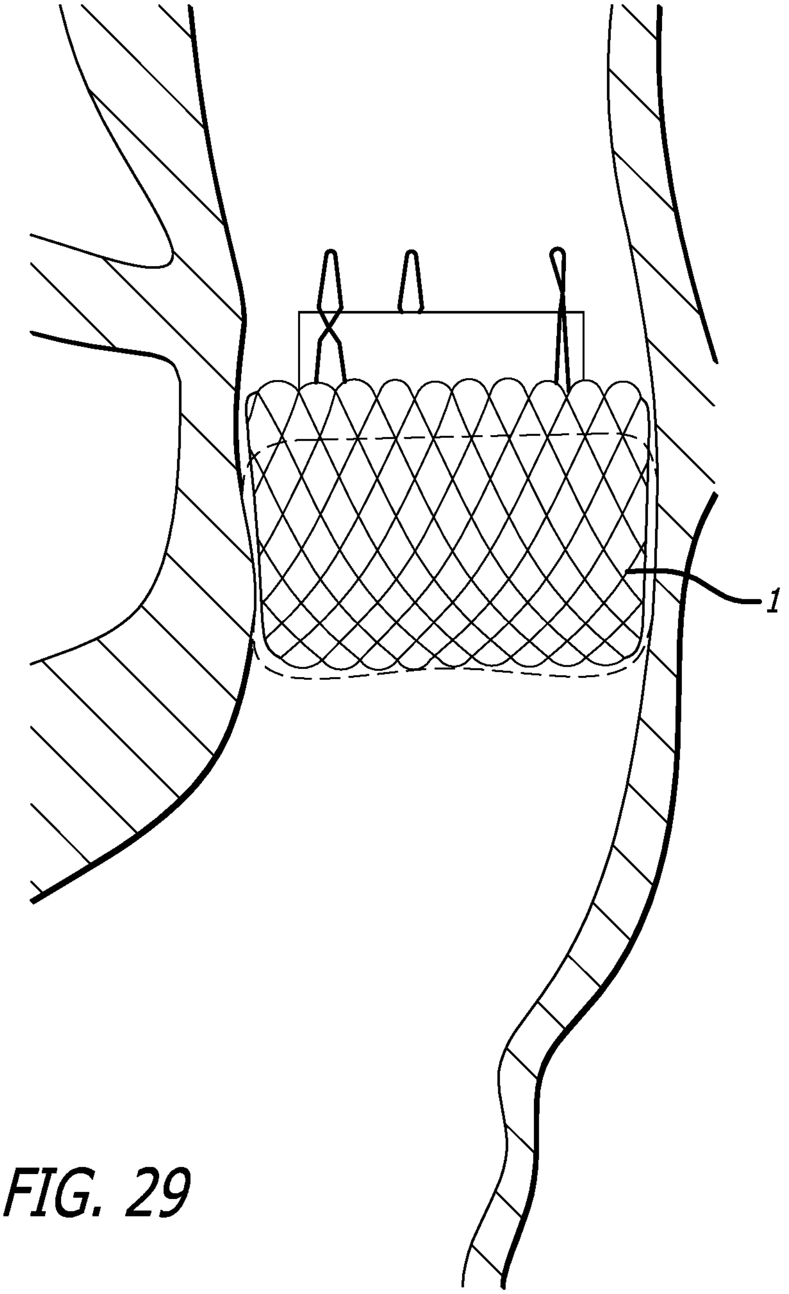

Finally, the delivery device 100 and guidewire 70 is removed from the patient, leaving only the functioning valve implant 1, as seen in FIG. 29.

Repositioning and recapturing of the implant has been described and can be seen as a significant advantage of the present system over other delivery systems on the market and being developed. The embodiments described above require manual steps which may be automated to a degree by alternative embodiments now described.

For example, as mentioned previously, FIG. 5 shows the initial stages of deployment of the implant 1. The target location has been reached and the delivery catheter 20 is retracted while the pusher catheter 30 and valve retention cables 40 remain stationary relative to the target location. Retracting the delivery catheter 20 causes the pusher catheter 30 to push the implant 1 out of the distal end 22 of the delivery catheter. As the implant 1 exits the delivery catheter 20 the implant 1 expands and the positioning mechanisms 60 are advanced through the delivery catheter 20 until the tethers 62 become taut.

Recall further that in FIG. 6, further advancement of the pusher catheter 30 causes implant material that is proximal of the connectors 64 to invert into the implant material that is distal of the connector 64. If repositioning of the implant is desired due to misplacement of the implant or suboptimal device orientation, the implant may be recaptured by reversing the rotation of the deployment dial, which drives a lead screw attached to the delivery catheter. However, if the positioning mechanism has been engaged and tightened onto the device, this tightening must be reversed in order to provide slack for the device to fully elongate and be recaptured into the catheter. Ideally, this slack provided is sufficient to elongate the device, but not further such that the connectors extend substantially beyond the end of the implant or impinge on the nosecone as it is drawn into the delivery catheter.

In one configuration, this slackening of the tension on the system may be provided by manually holding the tether positioning mechanism forward as the knob is rotated to recapture the implant. This maintains the forward position of the connectors as the valve is retracted. Importantly, the manual slackening of the connectors must be performed during the initial recapture of the implant but must then be stopped as the device is fully elongated to prevent over-extension of the tethers beyond the end of the implant. This is achieved using visual cues related to the appearance of the device via fluoroscopy to determine when slacking begins and ends.

A more automated embodiment allows this slackening of the tension is automated such that the decision points as to initiation and termination of slacking are controlled by the delivery system itself without input from the system user. Predetermined set points in the system control the engagement and disengagement of the tether control assembly related to the linear displacement of the device within the system.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for delivering an implant to a target location comprising:

providing a valve implant with leaflets and commissural points and a delivery device having a number of tethers with release mechanisms that corresponds to the commissural points;

connecting the tethers to the valve implant such that the tethers are aligned with the commissural points;

elongating and compressing the valve implant while loading the implant into a distal end of the delivery device;

navigating the distal end of the delivery device to a target location;

ejecting the valve implant from the distal end of the delivery device, allowing the valve implant to expand against the target site and reconfigure itself into a functional form;

observing full functionality of the leaflets prior to releasing the valve implant;

releasing the valve implant.

2. The method of claim 1 wherein connecting the tethers to the valve implant such that the tethers are aligned with the commissural points comprises connecting the tethers to loops formed in the ends of a wireform to which tissue is attached to form a valve of the valve implant.

3. The method of claim 1 wherein connecting the tethers to the valve implant comprises, for each of the tethers: retracting a sheath having a mouth at a distal end thereof, relative to a wire having a hook at a distal end thereof, such that the hook extends distally from the mouth, allowing a wire of the valve implant to be placed in the hook and become trapped between the hook and the mouth when the elastomeric sheath is released and the hook reenters the mouth.

4. The method of claim 1 further comprising pulling the valve implant back into the distal end of the delivery device if, after observing full functionality of the leaflets, the observed full functionality is unsatisfactory.

5. The method of claim 4 further comprising repeating the steps of navigating, ejecting, observing, and releasing.

6. The method of claim 1 wherein elongating and compressing the valve implant while loading the implant into a distal end of the delivery device comprises using the tethers and controls on the delivery device to draw the implant into the distal end of the delivery device.

7. A method for loading an implant into a delivery device comprising:

attaching an implant to tethers of a delivery device near commissural points of the implant;

using controls on the delivery device to retract the tethers into a distal end of the delivery device until the implant is contained within the distal end of the delivery device in an elongated, compressed configuration.

8. The method of claim 7 further comprising elongating the implant prior to using controls on the delivery device to retract the tethers.

9. The method of claim 8 wherein elongating the implant comprises unfolding the implant.

10. The method of claim 7 wherein using controls on the delivery device comprises using controls on the delivery device that rotate a leadscrew associated with a handle of the delivery device.

11. The method of claim 7 wherein attaching the implant to the tethers of the delivery device comprises attaching the implant to three tethers of the delivery device near three commissural points of the implant.

12. The method of claim 7 wherein attaching the implant to the tethers of the delivery device comprises opening a connection mechanism on the end of each of the tethers and placing a wire loop into the connection mechanism and then closing the connection mechanism.

13. A method of delivering an implant to a target location comprising:

navigating a delivery device with an implant in a distal end thereof to a target location;

using a control on a handle of the delivery device to rotate a leadscrew of a drive mechanism that causes a delivery catheter of the delivery device to retract relative to a connection mechanism connecting the implant to the delivery device;

continuing to use the control until the implant self-expands out of the distal end into the target location;

observing full functionality of the implant prior to releasing the implant;

releasing the implant by disconnecting the connection mechanism from the implant if satisfied with the observed full functionality of the implant.

14. The method of claim 13 wherein disconnecting the connection mechanism from the implant comprises opening connectors located at distal ends of tethers that are attached at a distal end of the implant.

15. The method of claim 14 wherein opening connectors comprises extending a cable having a hooked end out of a slotted mouth, thus allowing a wire of the implant to be released from the mouth.

16. The method of claim 15 wherein a slot of the slotted mouth and the hooked end of the cable together form a closed transverse passage that may trap the wire of the implant therein when closed, and wherein allowing the wire of the implant to be released comprises opening the transverse passage by advancing the cable distally such that the hook exits the mouth.

17. The method of claim 13 further comprising pulling the implant back into the distal end of the delivery device if the observed full functionality of the implant is unsatisfactory.

18. The method of claim 17 further comprising repeating the steps of claim 13 until satisfied with the observed full functionality of the implant.

19. The method of claim 17 wherein pulling the implant back into the distal end of the delivery device causes the implant to unfold and compress.

20. The method of claim 13 wherein when the implant self-expands out of the distal end into the target location, the implant also folds into itself and forms a prosthetic valve.

* * * * *